US006600073B1

(12) United States Patent
Schwartz et al.

(10) Patent No.: US 6,600,073 B1
(45) Date of Patent: Jul. 29, 2003

(54) METHODS FOR PREPARATION OF SERTRALINE HYDROCHLORIDE POLYMORPHS

(75) Inventors: Eduard Schwartz, Rechovot; Tamar Nidam, Yehud; Anita Liberman, Tel-Aviv; Marioara Mendelovici, Rechovot; Judith Aronhime, Rehovot; Claude Singer, Kfar Saba; Evgeni Valdman, Petah Tikva, all of (IL)

(73) Assignee: Teva Pharmaceutical Industries Ltd., Petah Tiqva (IL)

( * ) Notice: Subject to any disclaimer, the term of this patent is extended or adjusted under 35 U.S.C. 154(b) by 0 days.

(21) Appl. No.: 09/586,842

(22) Filed: Jun. 5, 2000

Related U.S. Application Data

(63) Continuation-in-part of application No. 09/448,985, filed on Nov. 24, 1999.

(51) Int. Cl.[7] ............................................. C07C 211/00
(52) U.S. Cl. ....................................................... 564/308
(58) Field of Search ......................................... 564/308

(56) References Cited

U.S. PATENT DOCUMENTS

| | | |
|---|---|---|
| 4,536,518 A | 8/1985 | Welch, Jr. et al. |
| 5,082,970 A | 1/1992 | Braish |
| 5,248,699 A | 9/1993 | Sysko et al. |
| 5,463,126 A | 10/1995 | Williams |
| 5,734,083 A | 3/1998 | Wilson et al. |
| 6,452,054 B2 | 9/2002 | Aronhime et al. |

FOREIGN PATENT DOCUMENTS

| | | |
|---|---|---|
| JP | 2000-26378 | 1/2000 |
| JP | 2000-26379 | 1/2000 |
| WO | WO 99/47486 | 9/1999 |
| WO | WO01/90049 | 11/2001 |

OTHER PUBLICATIONS

G.M. Wall, "Pharmaceutical Applications of Drug Crystal Studies", *Pharmaceutical Manu*facturing, vol. 3, No. 2, pp. 33–42, Feb. 1986.

J.K. Haleblian and W. McCrone, "*Pharmaceutical Applications of Polymorphism*" *Journal of Pharmaceutical Sciences*, vol. 58, No. 8, pp. 911–929, Aug. 1969.

J.K. Haleblian, "Characterization of Habits and Crystalline Modification of Solids and Their Pharmaceutical Applications", *Journal of Pharmaceutical Sci*ences, vol. 64, No. 8, pp. 1269–1288, Jul. 1975.

Welch, et al., "*Nontriczlic Antidepressant Agents Derived from cis–and trans–1–Amino–4–aryltetralins*", *Journal of Medicinal Chemistry*, vol. 27, No. 11, pp. 1508–1515, Feb. 14, 1984.

*Primary Examiner*—Samuel Barts
(74) *Attorney, Agent, or Firm*—Kenyon & Kenyon

(57) ABSTRACT

Novel methods for the preparation of sertraline hydrochloride Forms III, V, VI, VII, VII, IX and X are disclosed. According to the present invention, sertraline hydrochloride Form III may be produced by heating sertraline hydrochloride Forms V and VI. Sertraline hydrochloride Forms V and VI may be produced from either sertraline hydrochloride or sertraline base by crystallization. Sertraline hydrochloride Form VII may be produced by suspending sertraline chloride polymorph V in water, followed by filtration. Sertraline hydrochloride Forms VIII and IX may be produced by suspending sertraline base in water followed by acidification and filtration. Sertraline hydrochloride Form X may be produced by suspending sertraline hydrochloride in benzyl alcohol with heating, followed by filtration.

29 Claims, 16 Drawing Sheets

METHODS FOR PREPARATION OF SERTRALINE HYDROCHLORIDE POLYMORPHS

CROSS-REFERENCE TO RELATED APPLICATIONS

This application is a continuation-in-part of copending application Ser. No. 09/448,985 filed Nov. 24, 1999, the contents of which are incorporated by reference.

FIELD OF THE INVENTION

The present invention relates to novel, reproducible methods for the preparation of crystalline forms of sertraline hydrochloride Forms III and V through X, as well as the preparation of an amorphous form of sertraline hydrochloride.

BACKGROUND OF THE INVENTION

Sertraline hydrochloride, (1S-cis)-4-(3,4 dichlorophenyl)-1,2,3,4-tetrahydro-N-methyl-1-naphthalenamine hydrochloride, having the formula

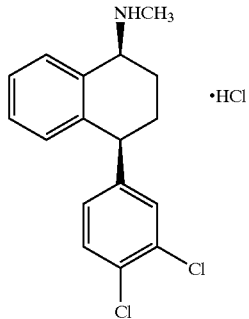

is approved, under the trademark Zoloft®, by the U.S. Food and Drug Administration, for the treatment of depression, obsessive-compulsive disorder and panic disorder.

U.S. Pat. No. 4,536,518 ("the '518 patent") describes the preparation of sertraline hydrochloride with a melting point of 243–245° C., by treating an ethyl acetate/ether solution of the free base with gaseous hydrogen chloride. The solid state properties of the sertraline hydrochloride so produced are not otherwise disclosed.

According to U.S. Pat. No. 5,248,699 ("the '699 patent"), the sertraline hydrochloride produced by the method of the '518 patent has a crystalline form denominated "Form II." The '699 patent discloses four other polymorphs I, III, IV, and V, and characterizes them by single crystal x-ray analysis, powder x-ray diffraction, infra-red spectroscopy, and differential scanning calorimetry. The '699 patent reports that Form II is produced by rapid crystallization of sertraline hydrochloride from an organic solvent, including isopropyl alcohol, ethyl acetate or hexane, and generally describes methods for making sertraline hydrochloride Forms I–V. According to this patent, the preferential formation of Forms I, II or IV in an acidic solution consisting of isopropyl alcohol, hexane, acetone, methyl isobutyl ketone, glacial acetic acid or, preferably, ethyl acetate, depends on the rapidity of crystallization. Form I is described as being made by crystallizing sertraline hydrochloride in an acidic solution using an organic solvent such as those listed above. The crystallization of Form I is carried out at a temperature from about 20° C. to about the solvent reflux temperature, preferably from about 40° to 60° C. The only method described in this patent for making Forms II and IV is by the rapid crystallization of sertraline hydrochloride from an organic solvent such as those listed above. Slow crystallization or granulation of sertraline hydrochloride is said to produce Form I. Form III is described as being formed by heating Forms I, II or IV to temperatures above about 180° C. Granulating either of Forms II, III or IV in any of the solvents listed above at a temperature from about 40° C. to 60° C. is said to cause conversion to Form I. The only method described in this patent for making Form V is by sublimation of sertraline hydrochloride Form I at reduced pressure and at a temperature from about 180–190° C. However, in our hands attempts to repeat this procedure to obtain Form V have been unsuccessful.

SUMMARY OF THE INVENTION

The present invention relates to a process for making sertraline hydrochloride Form V comprising the steps of: dissolving or suspending sertraline hydrochloride in a suitable solvent; removing the solvent; and drying to form sertraline hydrochloride Form V.

The present invention also relates to a process for making sertraline hydrochloride Form V comprising the steps of: dissolving or suspending sertraline base in a solvent; adding hydrogen chloride to the solvent to reduce the pH of the solution or suspension; and isolating sertraline hydrochloride Form V from the solution or suspension.

The present invention also relates to a process for making sertraline hydrochloride Form V comprising the step of drying sertraline hydrochloride Form VII.

The present invention also relates to a process for making sertraline hydrochloride Form V comprising the steps of: dissolving or suspending sertraline hydrochloride in water; adding a sufficient amount of hydrochloric acid or hydrogen chloride to facilitate precipitation of sertraline hydrochloride; removing the water; and isolating sertraline hydrochloride Form V.

The present invention also relates to a process for making sertraline hydrochloride Form VI comprising the steps of: dissolving sertraline base in a solvent; adding hydrochloric acid to the solvent; and isolating sertraline hydrochloride Form VI without further drying.

The present invention also relates to a process for making sertraline hydrochloride Form VI comprising the steps of: dissolving or suspending sertraline hydrochloride in ethanol or methanol; stirring for a time sufficient to induce the transformation of sertraline hydrochloride to sertraline hydrochloride Form VI; and isolating sertraline hydrochloride Form VI.

The present invention also relates to a process for making sertraline hydrochloride Form VIII comprising the steps of: suspending sertraline base in water; adding hydrogen chloride to the water; and filtrating the precipitate so obtained without further drying.

The present invention also relates to a process for making sertraline hydrochloride Form VIII comprising the steps of: suspending or dissolving sertraline hydrochloride ethanolate Form VI or sertraline hydrochloride Form II in water or a mixture of water and isopropyl alcohol; and isolating sertraline hydrochloride Form VIII.

The present invention also relates to a process for making sertraline hydrochloride Form III comprising the steps of: heating sertraline hydrochloride Form V or Form VI to a temperature sufficient, and for a time sufficient, to induce the transformation of sertraline hydrochloride Form V or Form VI to sertraline hydrochloride Form III; and isolating sertraline hydrochloride Form III.

The present invention also relates to a process for making amorphous sertraline hydrochloride comprising the steps of: suspending or dissolving sertraline base in a non-polar organic solvent; adding gaseous hydrochloric acid; and isolating amorphous sertraline hydrochloride.

DETAILED DESCRIPTION OF THE INVENTION

Form V

Figure 1:
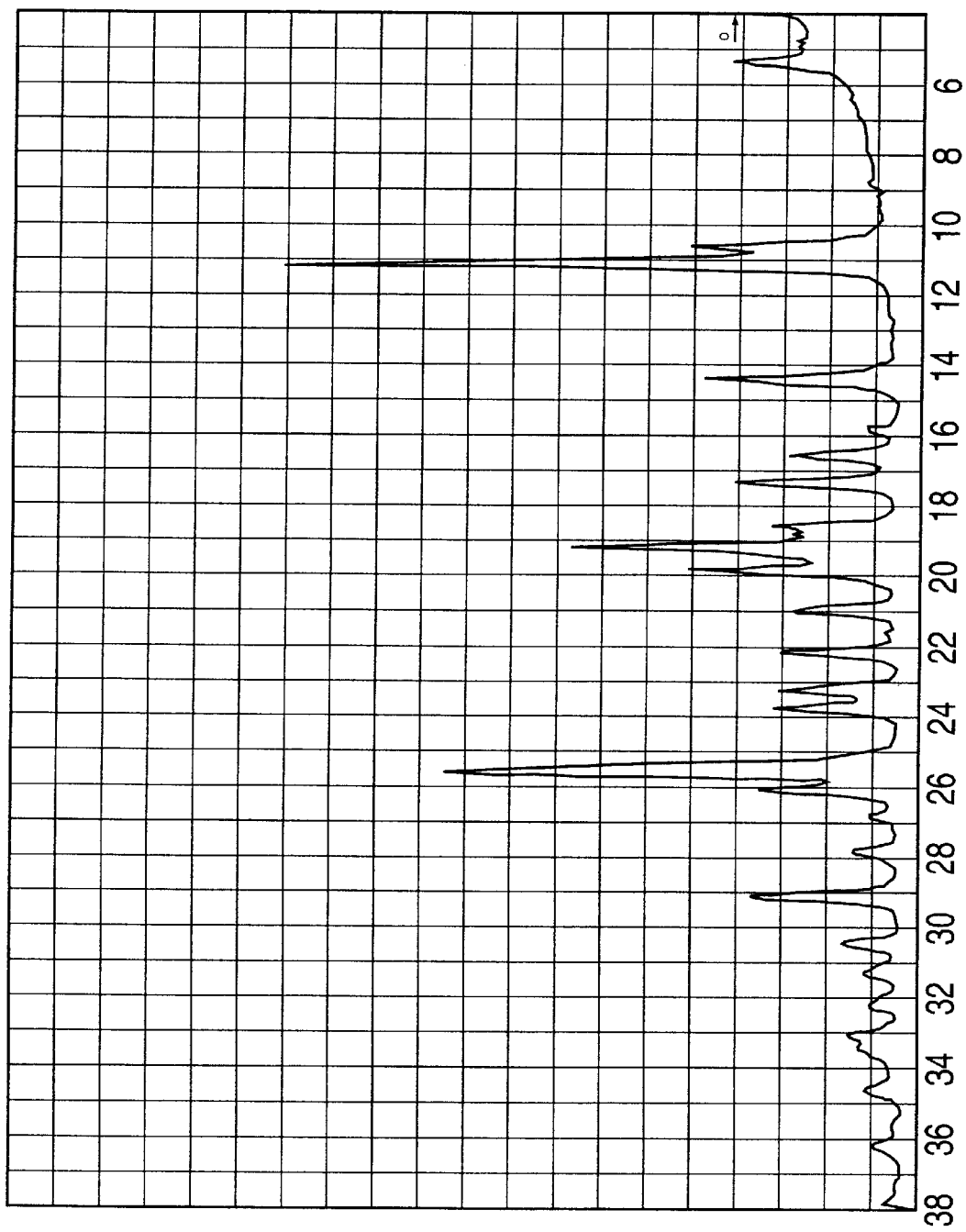
FIG. 1 is a characteristic x-ray powder diffraction spectrum of sertraline hydrochloride Form V.

The present invention provides new processes for making sertraline hydrochloride Form V from sertraline hydrochloride, sertraline base or amorphous sertraline hydrochloride. The methods provided in the present invention are more commercially practicable than the sublimation-condensation method of U.S. Pat. No. 5,248,699, which we have not been able to reproduce. It has also surprisingly been found that, by the present method, Form V is formed even at different crystallization rates.

Where the present invention provides methods for the conversion of sertraline hydrochloride to sertraline hydrochloride Form V, in one embodiment sertraline hydrochloride is combined with a solvent. Suitable solvents include methanol, ethanol, 1-methoxy-2-propanol, trichloroethane, water, and mixtures thereof. If a mixture of isopropyl alcohol and water is used, it is preferably an about 6:1 mixture. Preferably the solvent is methanol, ethanol, or mixtures thereof, and most preferably the solvent is ethanol. Sertraline hydrochloride Form V is then isolated by allowing the solution to cool. One preferred method is to rapidly cool the solvent to 5° C. Another preferred method comprises seeding the solution with sertraline hydrochloride Form V crystals, followed by slow cooling to room temperature, followed by filtration and drying.

Alternatively, Form V may be obtained by forming a solution or suspension of sertraline hydrochloride in a suitable solvent and spray drying the solution or suspension. Preferred solvents include water and water/alcohol mixtures.

The present invention also provides methods for the conversion of sertraline hydrochloride to sertraline hydrochloride Form V wherein the solvate sertraline hydrochloride Form VI (described in more detail below) is an intermediate. In this embodiment of the present invention, sertraline hydrochloride is suspended or dissolved in either methanol or ethanol or mixtures thereof thereby forming sertraline hydrochloride Form VI. This intermediate sertraline hydrochloride Form VI is then dried, with or without a separate isolation step, to remove all solvent and sertraline hydrochloride Form V is isolated. Sertraline hydrochloride Form V can also be prepared by suspending or dissolving sertraline hydrochloride solvate Form VI in water.

Sertraline hydrochloride Form V can also be prepared by drying Form VII (described in more detail below). In this embodiment of the present invention, sertraline hydrochloride Form V is dried at 80° C. overnight thereby forming sertraline hydrochloride Form V.

The present invention also provides methods for the conversion of sertraline hydrochloride to sertraline hydrochloride Form V wherein the sertraline hydrochloride Form VIII (described in more detail below) is an intermediate. In this embodiment of the present invention, sertraline hydrochloride Form II is suspended or dissolved in water thereby forming sertraline hydrochloride Form VIII. This intermediate sertraline hydrochloride Form VIII is then dried, with or without a separate isolation step, to remove all solvent and sertraline hydrochloride Form V is isolated. Methods for the preparation of sertraline hydrochloride Form II are disclosed in copending applications serial Nos. 09/448,985 filed Nov. 24, 1999 and attorney docket number 1662/49107, filed May 22, 2000, the contents of which are hereby incorporated by reference.

The present invention also provides methods for the conversion of sertraline base to sertraline hydrochloride Form V. In one such embodiment, sertraline base is added to at least one solvent, and hydrogen chloride gas is bubbled through the solution. Suitable solvents include methanol, ethanol, water, ethyl acetate, isopropyl alcohol, ether, hexane, and toluene, and mixtures thereof. Alternatively, an appropriate amount of hydrogen chloride gas dissolved in a suitable solvent and then combined with the sertraline base solution. As used herein, "hydrogen chloride" includes both gaseous hydrogen chloride and aqueous hydrogen chloride (i.e. hydrochloric acid). Sertraline hydrochloride Form V is isolated by allowing precipitation to occur from about 0° C. to about 60° C. followed by filtration and drying. Preferred solvents include methanol, ethanol, hexane, isopropyl alcohol, or mixtures thereof. In a variation of this method, sertraline base is added to a suitable solvent and the resulting solution is added to a hydrochloric acid solution of pH 0–4; preferably the pH of the solution is about 1.

Alternatively, sertraline base is added to a solvent. The solution is heated and concentrated hydrochloric acid is added. Water may also be added. The solvent may be partially removed by distillation. Sertraline hydrochloride Form V is isolated by allowing the mixture to cool to room temperature and remain at room temperature overnight, followed by filtration and drying. Suitable solvents for use in this method include methanol, ethanol, water, hexane, isopropyl alcohol, and ethyl acetate, and mixtures thereof.

Alternatively, sertraline base may be combined with a solvent selected from the group consisting of methanol, ethanol and a mixture thereof. A saturated solution of hydrogen chloride gas in isopropyl alcohol is added to induce formation of sertraline hydrochloride Form V. Sertraline hydrochloride Form V is isolated by allowing the solution to stand at room temperature overnight, followed by filtration and drying of the precipitate.

Form V may also be obtained by forming a suspension of sertraline base and hydrochloric acid in water or a water/ethanol mixture and spray drying the suspension. In this embodiment of the present invention, the solution or suspension of sertraline base and hydrochloric acid is sprayed into a heated chamber. The temperature of the chamber is such that the solvent is removed thus forming sertraline hydrochloride Form V.

Sertraline base for use in the processes of the present invention may be produced by dissolving sertraline mandelate in ethyl acetate followed by neutralization of the sertraline mandelate with aqueous sodium hydroxide. The organic phase is separated from the aqueous phase and dried using magnesium sulfate. The solvent is removed under reduced pressure to produce sertraline base as an oil. Methods for making sertraline base are set forth in U.S. Pat. Nos. 4,536,518 and 5,248,699, the contents of which are incorporated herein by reference.

Where the present invention provides methods for the conversion of amorphous sertraline hydrochloride to sertraline hydrochloride Form V, amorphous sertraline hydrochloride is kept in a closed container, such as a bag, and warmed to about 40° C. to about 80° C. or is stored at room temperature for a period between a few hours and several days depending on the temperature.

The sertraline hydrochloride Form V that results from practicing the invention as exemplified herein can be characterized by its powder X-ray diffraction pattern. FIG. 1 is a representative pattern of sertraline hydrochloride Form V. The principal peaks observed are at about 5.2°±0.2, 10.4°±0.2, 11.0°±0.2, 14.3°±0.2, 16.5°±0.2, 17.3°±0.2, 18.4°±0.2, 19.1°±0.2, 19.7°±0.2, 20.9°±0.2, 22.0°±0.2, 23.2°±0.2, 23.6°±0.2, 25.5°±0.2, 26.0°±0.2, and 29.1°±0.2 degrees 2 theta.

Three experiments were performed in order to repeat the procedure described in U.S. Pat. No. 5,248,699 for preparing Form V by sublimation. Two experiments were performed by sublimating a sample of Form I under 30 mm Hg vacuum and temperature between 170–190° C. A third experiment was performed by sublimating a sample of Form I under high vacuum (0.1 mm Hg) and temperature between 180–195° C.

Figure 2:
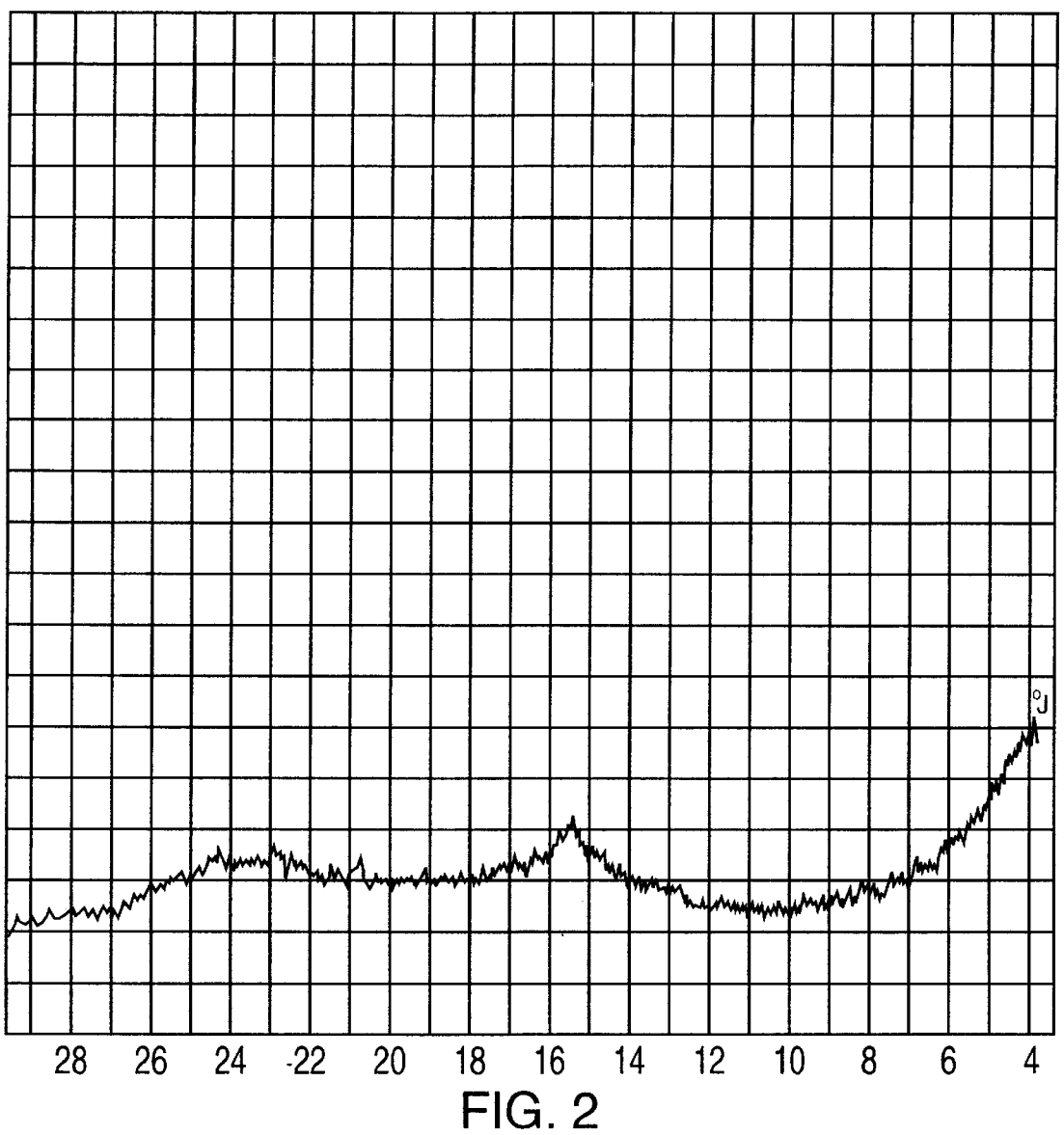
FIG. 2 is a characteristic x-ray powder diffraction spectrum of amorphous sertraline hydrochloride.

The three samples of sertraline hydrochloride prepared by sublimation were analyzed by powder x-ray diffraction. In all cases, the typical broad featureless pattern without sharp peaks typical of amorphous materials was obtained. FIG. 2 is one such pattern.

In conclusion, sertraline hydrochloride could not be obtained by following the procedure set forth in U.S. Pat. No. 5,248,699 for preparing Form V by sublimation of Form I.

Figure 4:
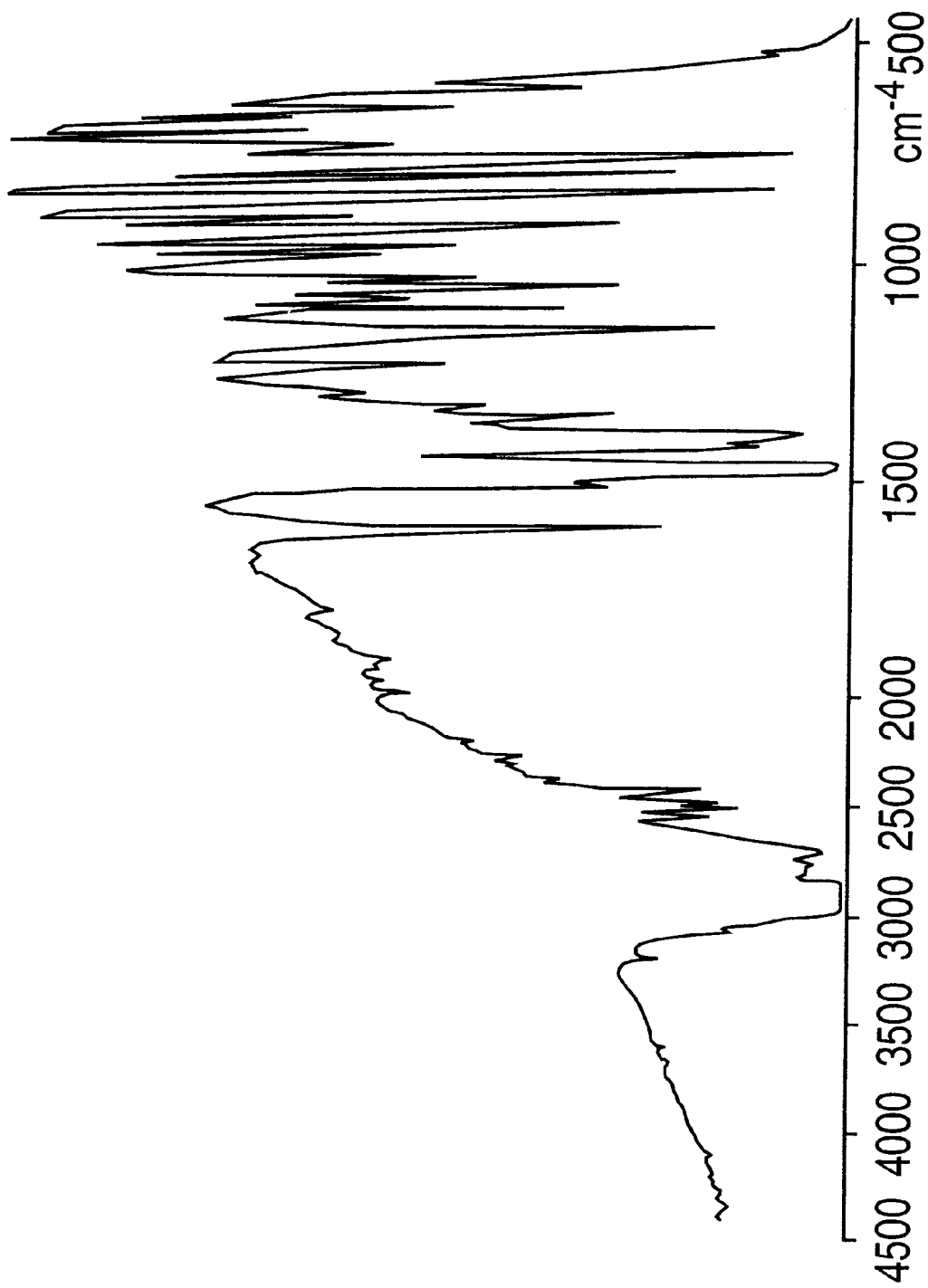
FIG. 4 is a characteristic infrared (IR) absorption spectrum of sertraline hydrochloride Form V.

The IR spectrum of sertraline hydrochloride Form V produced by the present process is characterized by the following bands: 773 cm$^{-1}$, 822 cm$^{-1}$, 1012 cm$^{-1}$, 1032 cm$^{-1}$, 1054 cm$^{-1}$, 1133 cm$^{-1}$, 1328 cm$^{-1}$, 1562 cm$^{-1}$, and 1590 cm$^{-1}$, as shown in FIG. 4.

Figure 3:
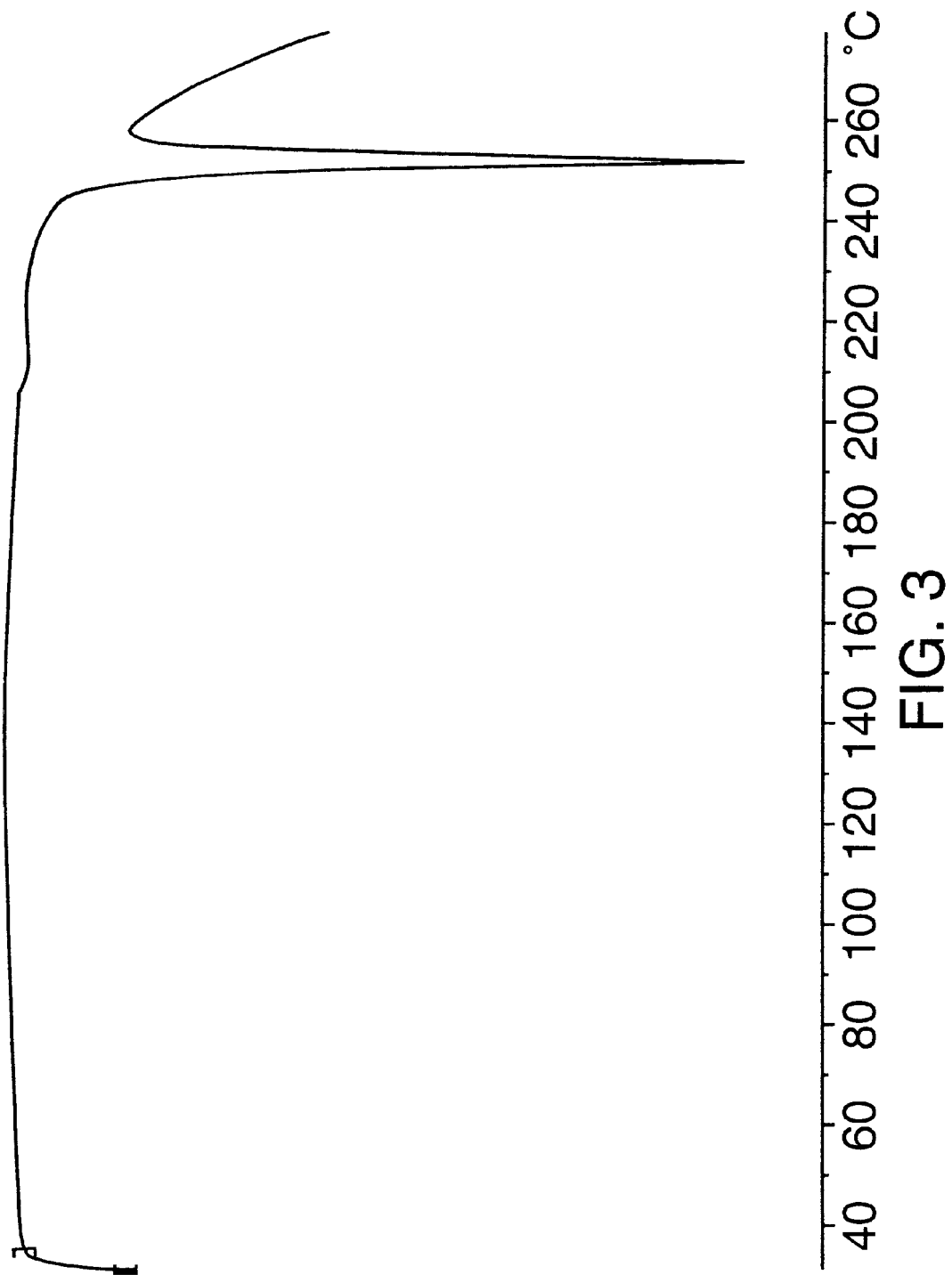
FIG. 3 is a characteristic differential scanning calorimetric (DSC) thermogram of sertraline hydrochloride Form V.

The sertraline hydrochloride Form V of the present process is further characterized by the DSC thermogram data, for example, as disclosed in FIG. 3. The DSC thermogram is characterized by a small endotherm (~3 Joule per gram) at about 210° C., believed to be a solid-solid transformation (based upon observation under a hot stage microscope) to Form III, and a melting peak 251° C.

Form VI

Sertraline hydrochloride Form VI is a solvated crystal form of sertraline hydrochloride. Sertraline hydrochloride Form VI may be an ethanolate, wherein ethanol is incorporated into the crystal structure of Form VI. Alternatively, sertraline hydrochloride Form VI may be a methanolate, wherein methanol is incorporated into the crystal structure of sertraline hydrochloride Form VI. All sertraline hydrochloride Form VI solvates have identical powder x-ray diffraction patterns. Therefore, when referring to sertraline hydrochloride Form VI all sertraline hydrochloride Form VI solvates, such as sertraline hydrochloride Form VI ethanolate and sertraline hydrochloride Form VI methanolate, are necessarily included.

Figure 13:
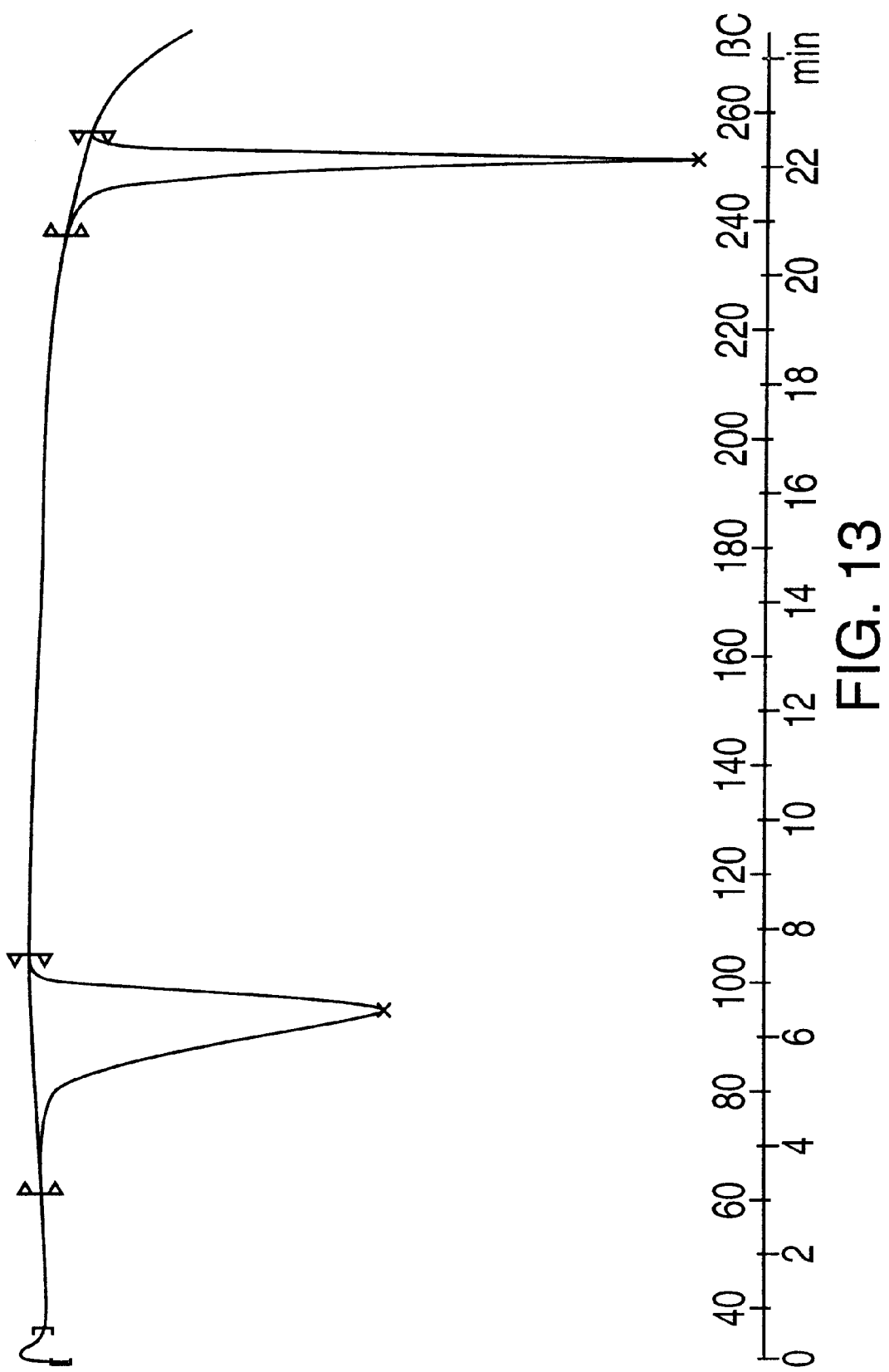
FIG. 13 is a characteristic differential scanning calorimetric (DSC) thermogram of sertraline hydrochloride Form VI.

To form the novel crystalline form sertraline hydrochloride Form VI, sertraline base is added to the appropriate solvent. Which solvent is appropriate will depend on which solvate is to be formed, e.g. ethanol (to form the ethanolate) and methanol (to form the methanolate). Hydrogen chloride gas is then bubbled through the solution. Sertraline hydrochloride Form VI is isolated by allowing precipitation to occur, followed by filtration. The DSC thermogram of Form VI crystallized from ethanol displays a desolvation peak at 95° C. (see FIG. 13) and loses 11.2% weight (by TGA); Form VI crystallized from methanol loses 8.3 % weight (by TGA) upon desolvation. Form VI crystallized from ethanol is an ethanolate, and more specifically is a monoethanolate. Form VI crystallized from methanol is a methanolate, and more specifically is a monomethanolate.

The present invention also provides new processes for making sertraline hydrochloride solvate Form VI by reslurry of other sertraline hydrochloride crystalline forms. In the conversion of sertraline hydrochloride to sertraline hydrochloride ethanolate Form VI, sertraline hydrochloride is dissolved in the appropriate solvent and stirred for about 18–36 hours; 24 hours is preferred. Sertraline hydrochloride solvate Form VI is isolated by a suitable method, such as filtration. Sertraline hydrochloride Forms I, II, III IV, V and X are suitable for use as starting materials in this process.

Figure 5:
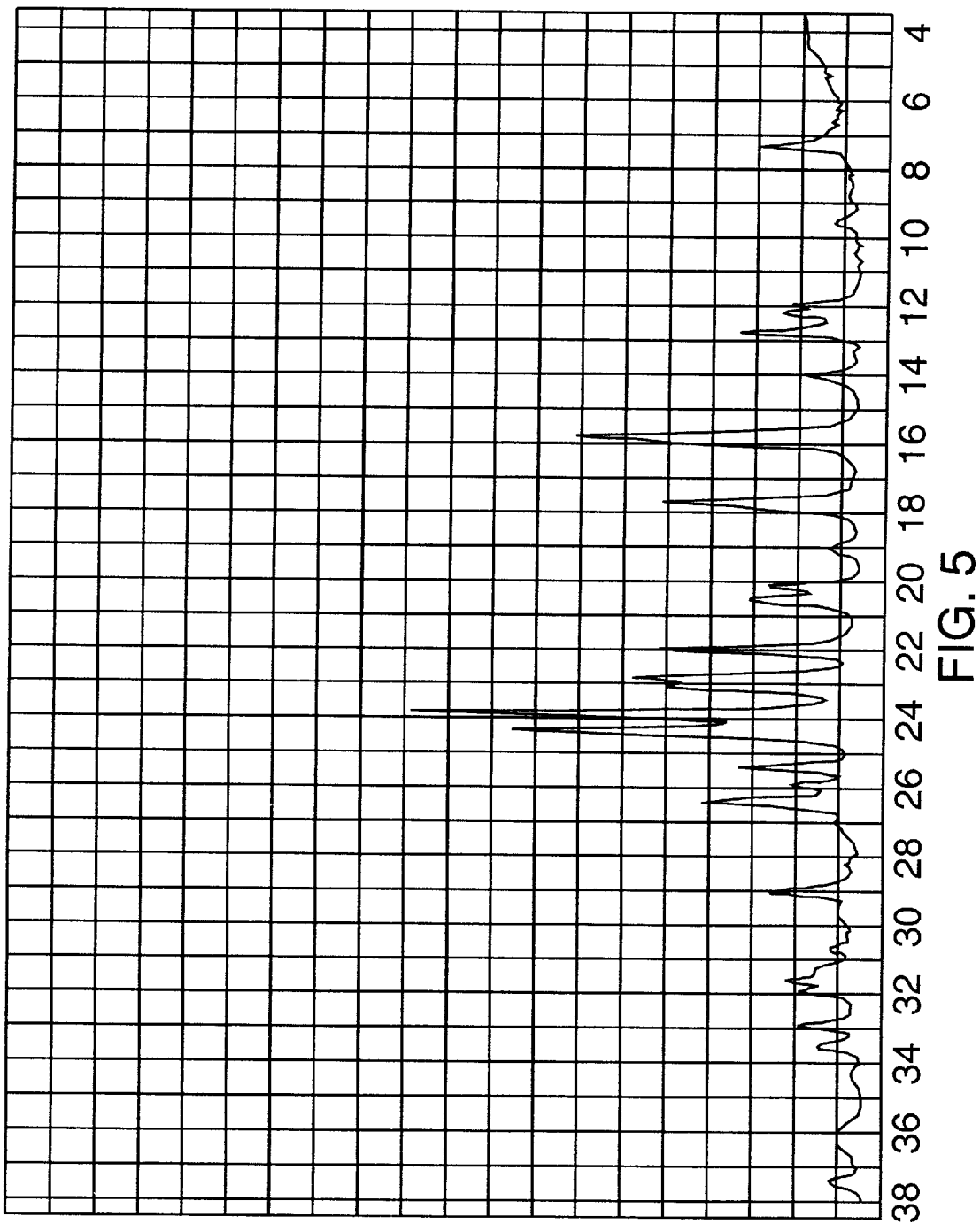
FIG. 5 is a characteristic x-ray powder diffraction spectrum of sertraline hydrochloride Form VI.

The sertraline hydrochloride Form VI so isolated is a solvate and exhibits the powder x-ray diffraction pattern of FIG. 5, comprising peaks at 7.3°±0.2, 12.1°±0.2, 12.7°±0.2, 14.0°±0.2, 15.6°±0.2, 17.6°±0.2, 20.1°±0.2, 20.6°±0.2, 21.9°±0.2, 22.7°±0.2, 23.0°±0.2, 23.8°±0.2, 24.3°±0.2, 25.4°±0.2, and 26.3°±0.2 degrees two-theta. Drying of the precipitated sertraline hydrochloride Form VI at 50–60° C. overnight yields sertraline hydrochloride Form V.

Form VII

It has also been discovered that a new crystalline form of sertraline hydrochloride, designated Form VII, may be obtained by suspending or dissolving Form V in water, and filtrating the suspension after one day without further drying.

In another embodiment of the invention, sertraline hydrochloride Form VII is made from sertraline hydrochloride Form VI. Sertraline hydrochloride Form VI is dispersed in water and the mixture is heated to facilitate the dissolution of sertraline hydrochloride Form VI. The solution may be heated to between about 30° C. and about 90° C., preferably to about 80° C. The pH is then lowered, preferably to about pH 1, and the mixture is allowed to cool to room temperature and stirred until the reaction is complete. Preferably the reaction is stirred for two hours at room temperature. Sertraline hydrochloride Form VII is isolated by filtration and washing with water.

Figure 6:
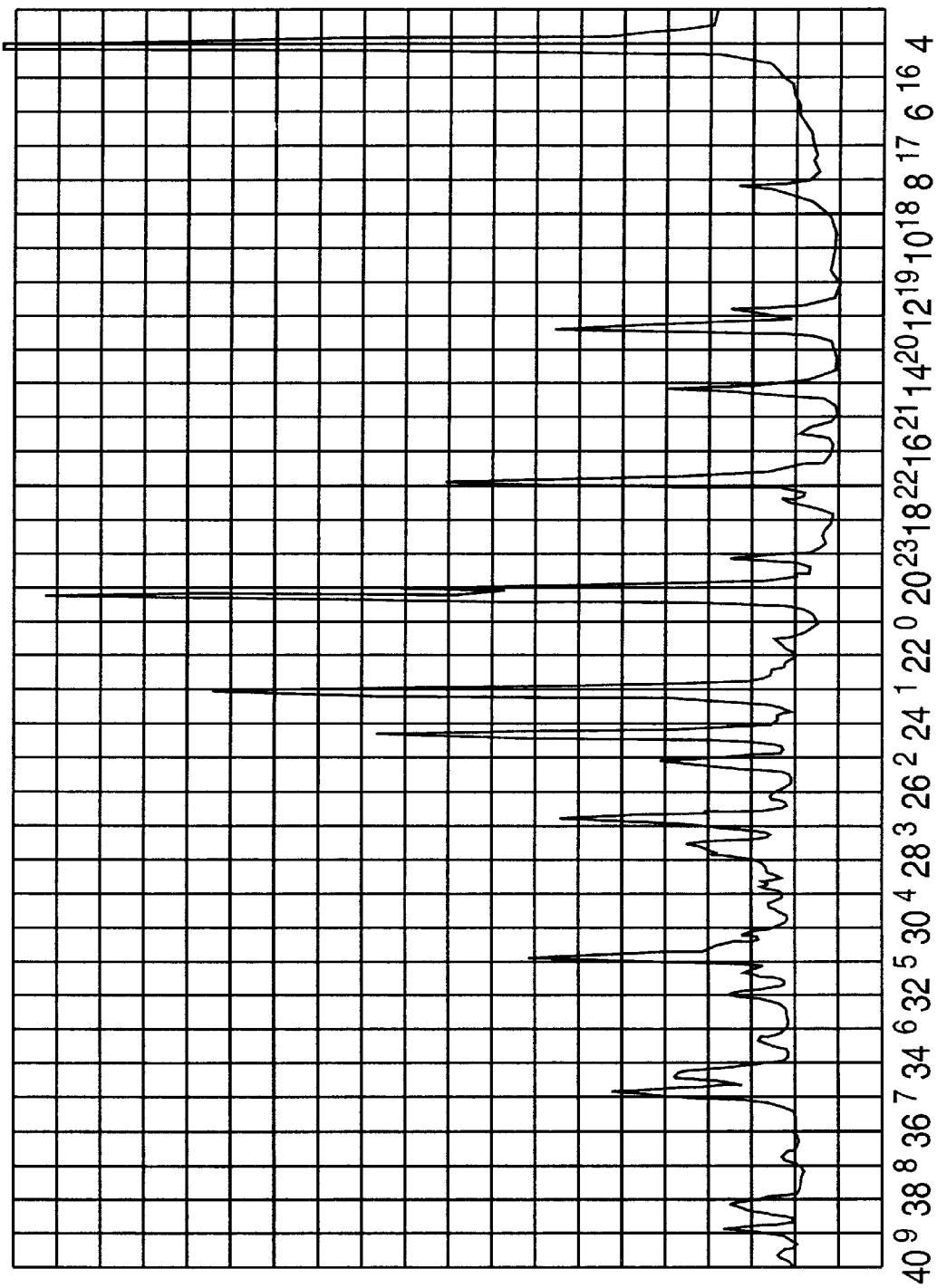
FIG. 6 is a characteristic x-ray powder diffraction spectrum of sertraline hydrochloride Form VII.

As shown in FIG. 6, sertraline hydrochloride Form VII is characterized by two unique strong x-ray powder diffraction peaks at 4.0°±0.2, and 20.0 degrees two-theta and medium intensity peaks at 8.0°±0.2, 11.6°±0.2, 12.0°±0.2, 13.8°±0.2, 16.5°±0.2, 22.8°±0.2, 24.1°±0.2, 25.0°±0.2, 26.6°±0.2, 30.7°±0.2, 34.7°±0.2 2 two-theta. The TGA curve shows a loss on drying of about 45%.

Forms VIII and IX

Additional new crystalline forms of sertraline hydrochloride, Forms VIII and IX, have also been discovered. Sertraline hydrochloride hydrate Form VIII may be produced by suspending sertraline base in water and heating, followed by acidification and filtration. Form IX is obtained by drying of Form VIII. Preferably the sertraline base is suspended in water, the suspension heated to a temperature between about 30° C. and about 80° C. Hydrogen chloride is added to reduce the pH, preferably to between about 1 to about 4, and the resulting solution is cooled to room temperature.

The present invention also provides new processes for making sertraline hydrochloride Form VIII from sertraline hydrochloride ethanolate Form VI. In one embodiment of the present invention, a slurry of sertraline hydrochloride ethanolate Form VI in water or a mixture of water and isopropyl alcohol is stirred, preferably for about one hour. The slurry is then filtered and washed with water and sertraline hydrochloride hydrate Form VIII is isolated.

The present invention also provides precesses of making sertraline hydrochloride Form VIII from sertraline hydrochloride Form II. In the conversion of sertraline hydrochloride Form II to sertraline hydrochloride Form VIII, sertraline hydrochloride Form II is suspended in water or a mixture of water and isopropyl alcohol and stirred, preferably overnight, and sertraline hydrochloride hydrate Form VIII is isolated by filtration.

Figure 7:
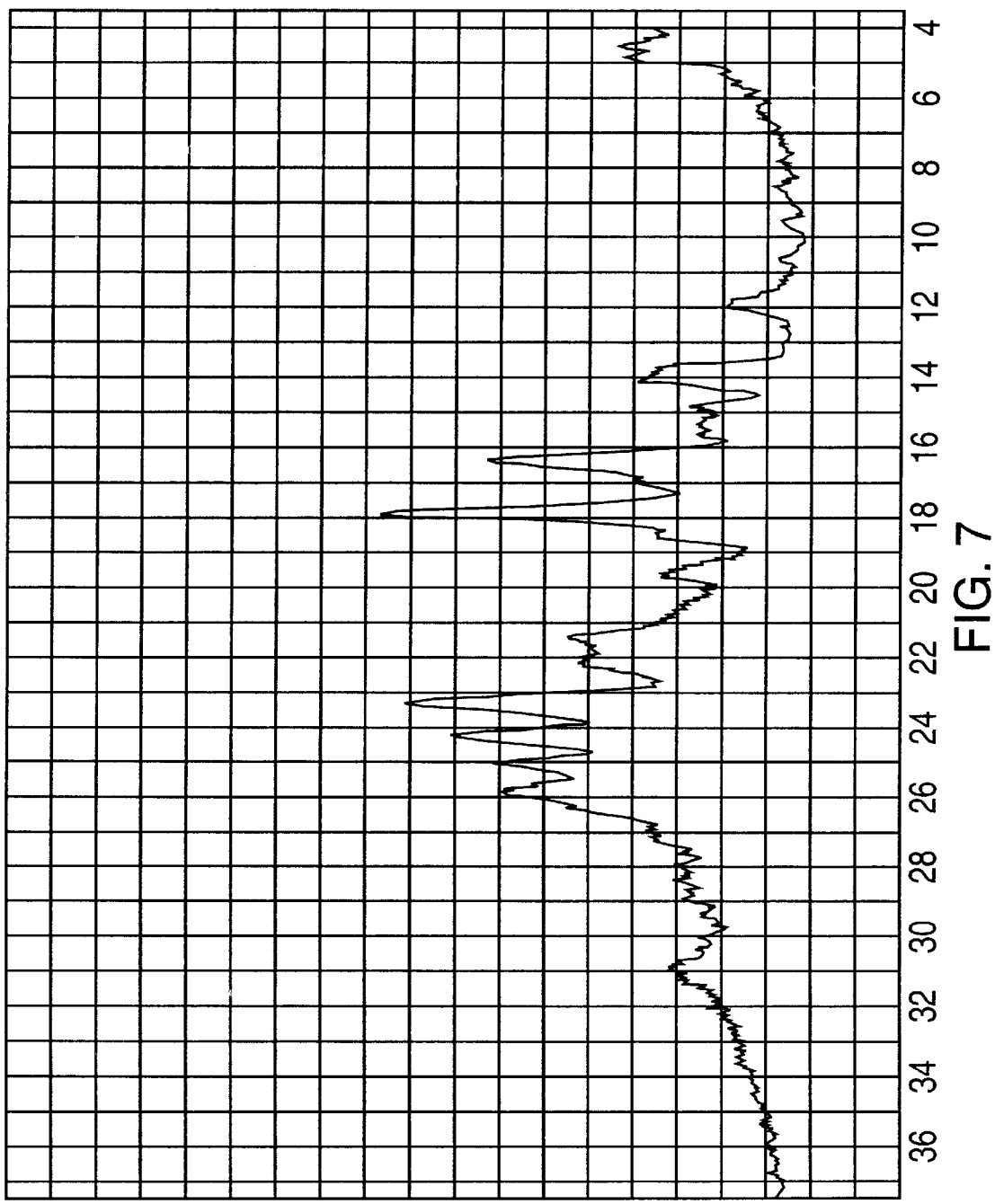
FIG. 7 is a characteristic x-ray powder diffraction spectrum of sertraline hydrochloride Form VIII.

Sertraline hydrochloride Form VIII is characterized by x-ray powder diffraction peaks at 4.7°±0.2, 11.8°±0.2, 16.3°±0.2, 17.8°±0.2, 19.6°±0.2, 23.2°±0.2, 24.2°±0.2, 25.1°±0.2, and 26.0°±0.2 two-theta, as described in FIG. 7.

Figure 9:
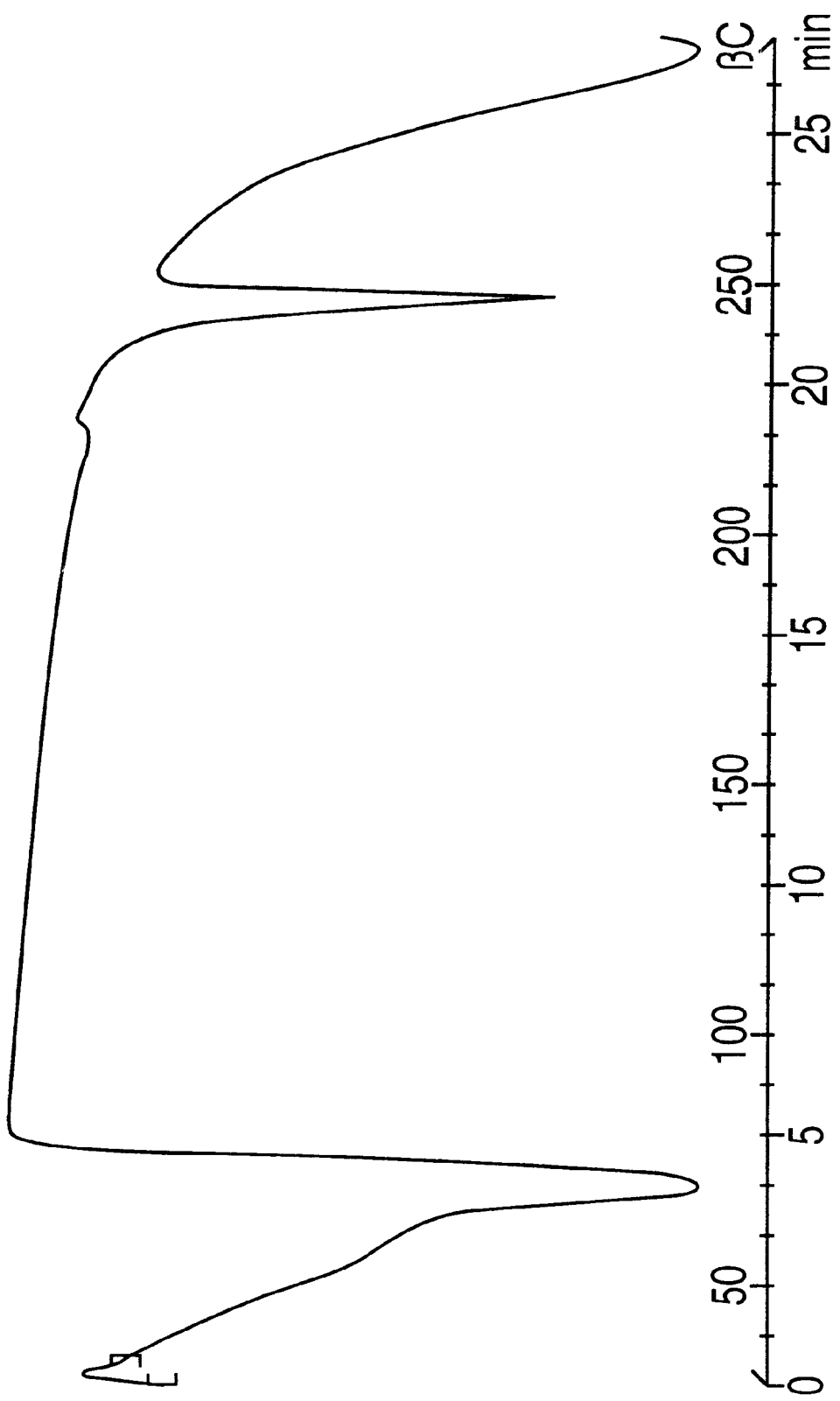
FIG. 9 is a characteristic differential scanning calorimetric (DSC) thermogram of sertraline hydrochloride Form VIII.

The DSC thermogram for Form VIII is characterized by a strong endotherm below 100° C., small endothermic and exothermic events at about 220° C. and a melting peak at 247° C. as described in FIG. 9.

The TGA curve shows a loss on drying step of about 20% below 100° C.

Figure 11:
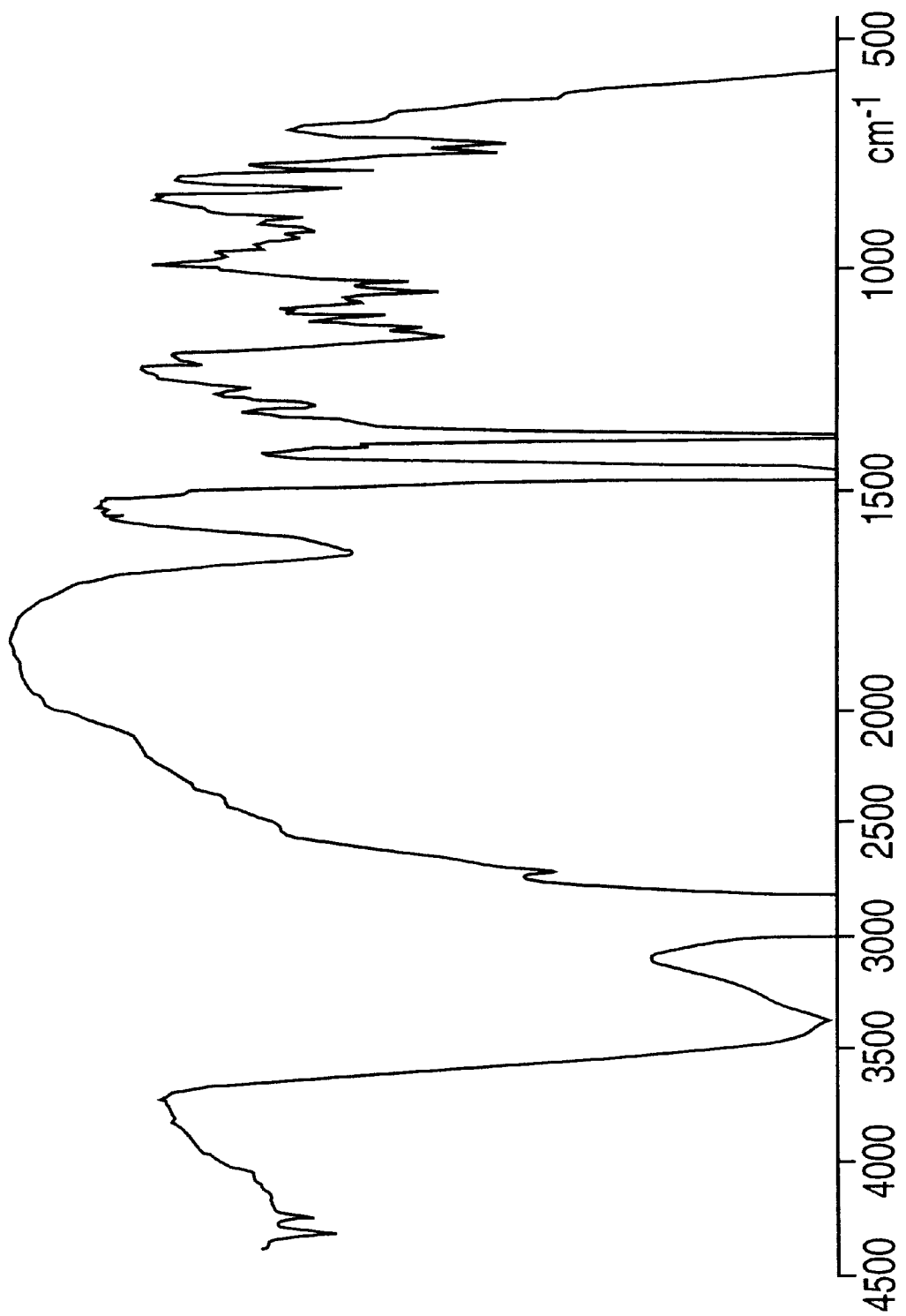
FIG. 11 is a characteristic infrared (IR) absorption spectrum of sertraline hydrochloride Form VIII.

The IR spectrum of Form VIII is characterized by the following bands: 740 $cm^{-1}$, 779 $cm^{-1}$, 822 $cm^{-1}$, 887 $cm^{-1}$, 915 $cm^{-1}$, 1031 $cm^{-1}$, 1053 $cm^{-1}$, 1110 $cm^{-1}$, 1134 $cm^{-1}$, 1153 $cm^{-1}$, 1217 $cm^{-1}$, 1307 $cm^{-1}$, and 1377 $cm^{-1}$, as described in FIG. 11.

Figure 8:
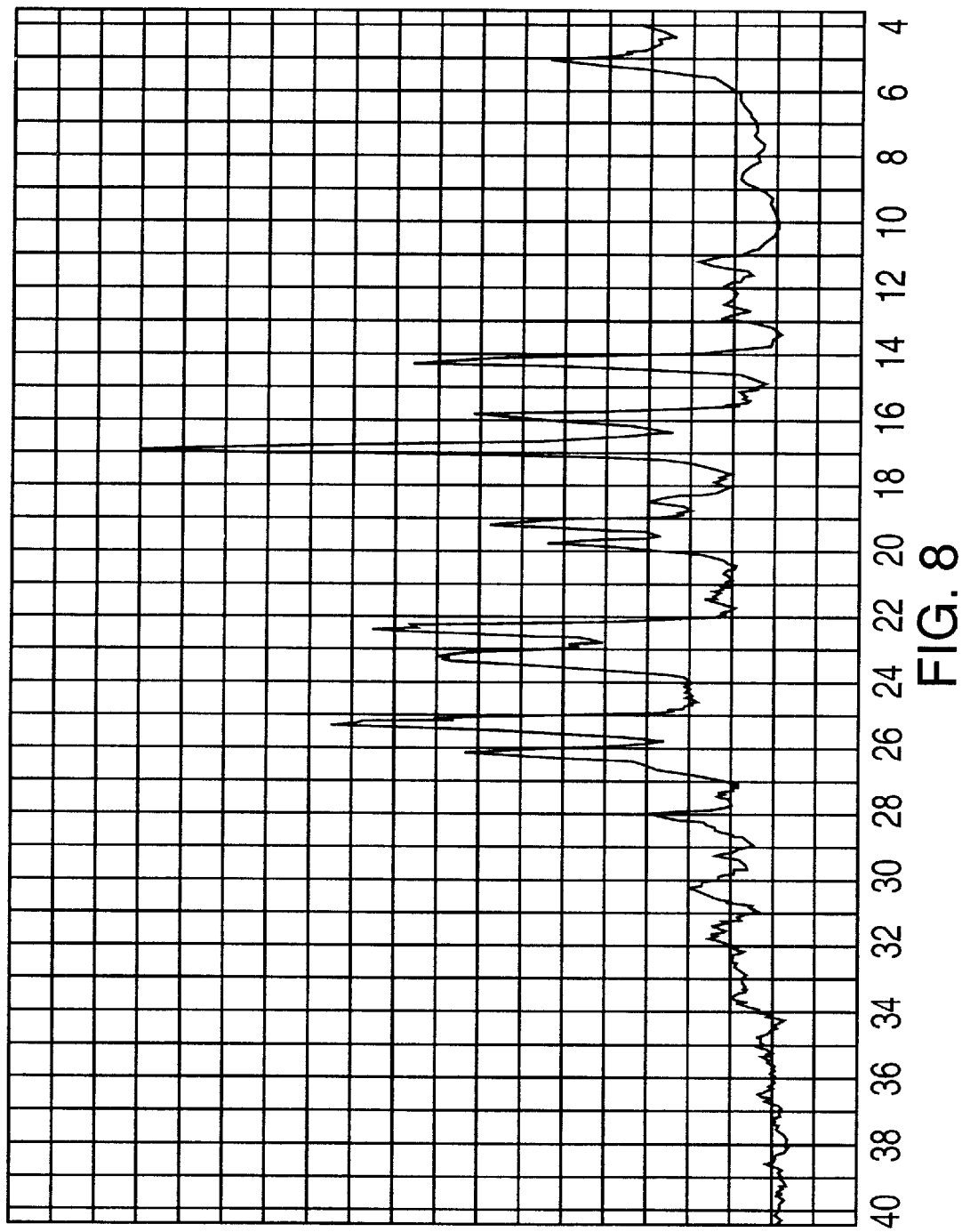
FIG. 8 is a characteristic x-ray powder diffraction spectrum of sertraline hydrochloride Form IX.

Sertraline hydrochloride Form IX is characterized by x-ray powder diffraction peaks at 5.1°±0.2, 14.2°±0.2, 15.8°±0.2, 16.8°±0.2, 19.2°±0.2, 19.7°±0.2, 22.4°±0.2, 23.2°±0.2, 25.3°±0.2 and 26.1°±0.2 two-theta, as described in FIG. 8.

Figure 12:
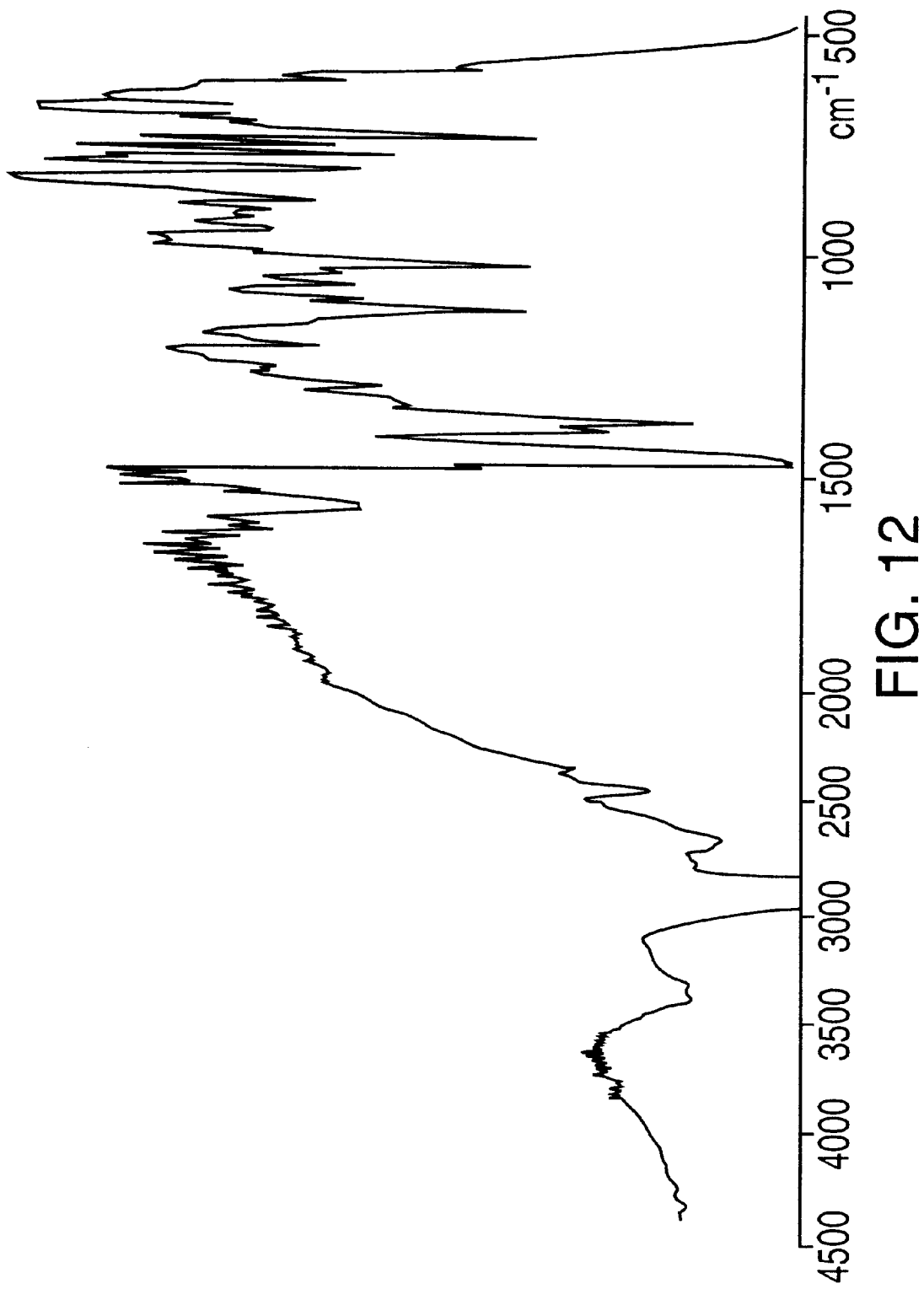
FIG. 12 is a characteristic infrared (IR) absorption spectrum of sertraline hydrochloride Form IX.

The IR spectrum of Form IX is characterized by the following bands: 701 $cm^{-1}$, 715 $cm^{-1}$, 741 $cm^{-1}$, 758 $cm^{-1}$, 780 $cm^{-1}$, 816 $cm^{-1}$, 823 $cm^{-1}$, 1030 $cm^{-1}$, 1053 $cm^{-1}$, 1078 $cm^{-1}$, 1110 $cm^{-1}$, 1204 $cm^{-1}$, 1217 $cm^{-1}$, 1307 $cm^{-1}$, and 1350 $cm^{-1}$, as described in FIG. 12.

Form X

It has further been discovered that another crystalline form of sertraline hydrochloride, denominated Form X may be obtained by suspending sertraline hydrochloride in benzyl alcohol, and heating to facilitate dissolution. The solution is cooled and the precipitate filtered, washed with benzyl alcohol and dried, to yield sertraline hydrochloride Form X.

Figure 14:
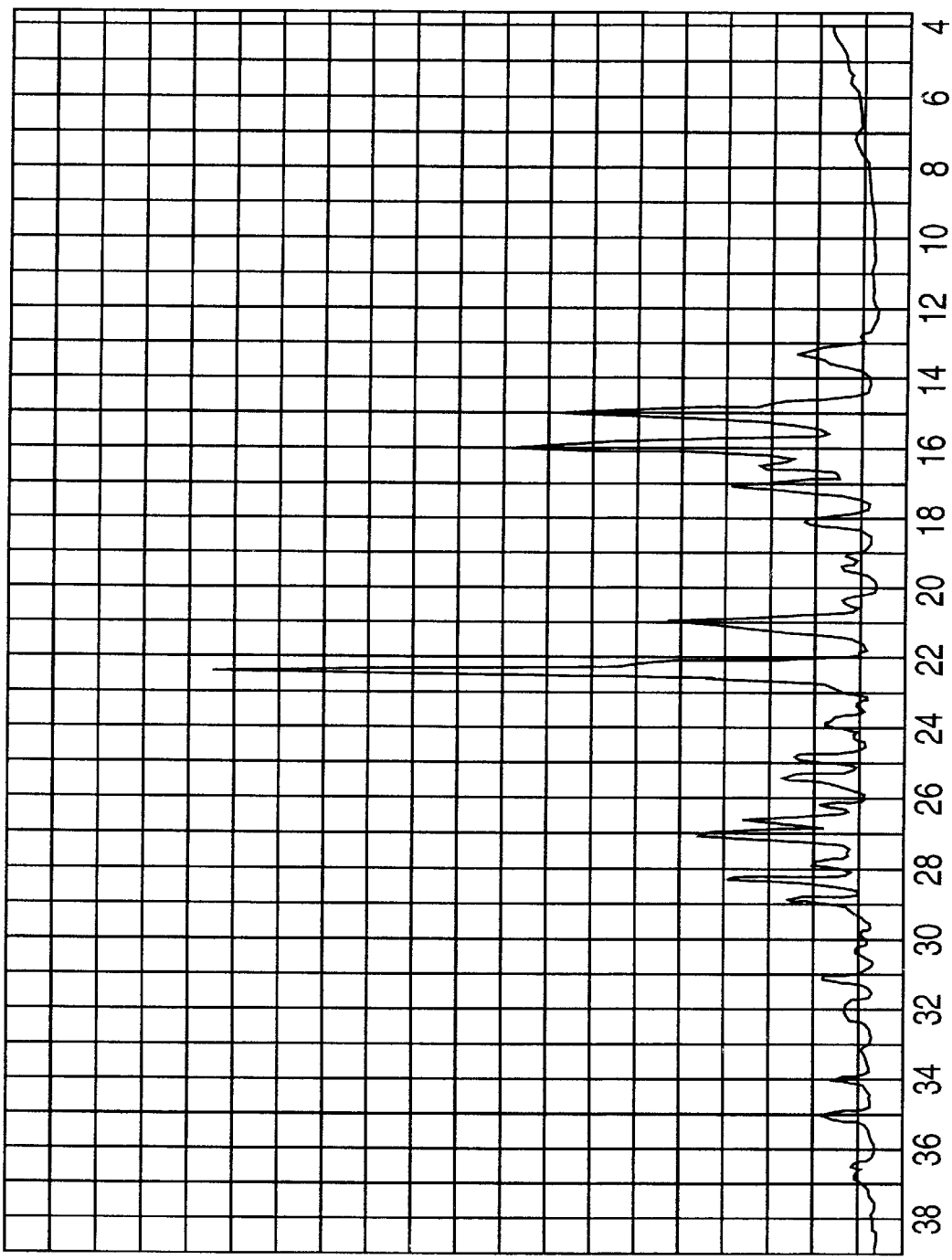
FIG. 14 is a characteristic x-ray powder diffraction spectrum of sertraline hydrochloride Form X.

The Form X produced in this manner is characterized by a powder x-ray diffraction pattern having its principal peaks at 15.0°±0.2, 16.0° 16.5°±0.2 17.0°±0.2, 18.1°±0.2, 21.0°±0.2, 22.4°±0.2, 24.9°±0.2, 25.4°±0.2, 26.2°±0.2, 27.1°±0.2, 28.4°±0.2, and 29.0°±0.2 degrees two-theta as described in FIG. 14.

Figure 15:
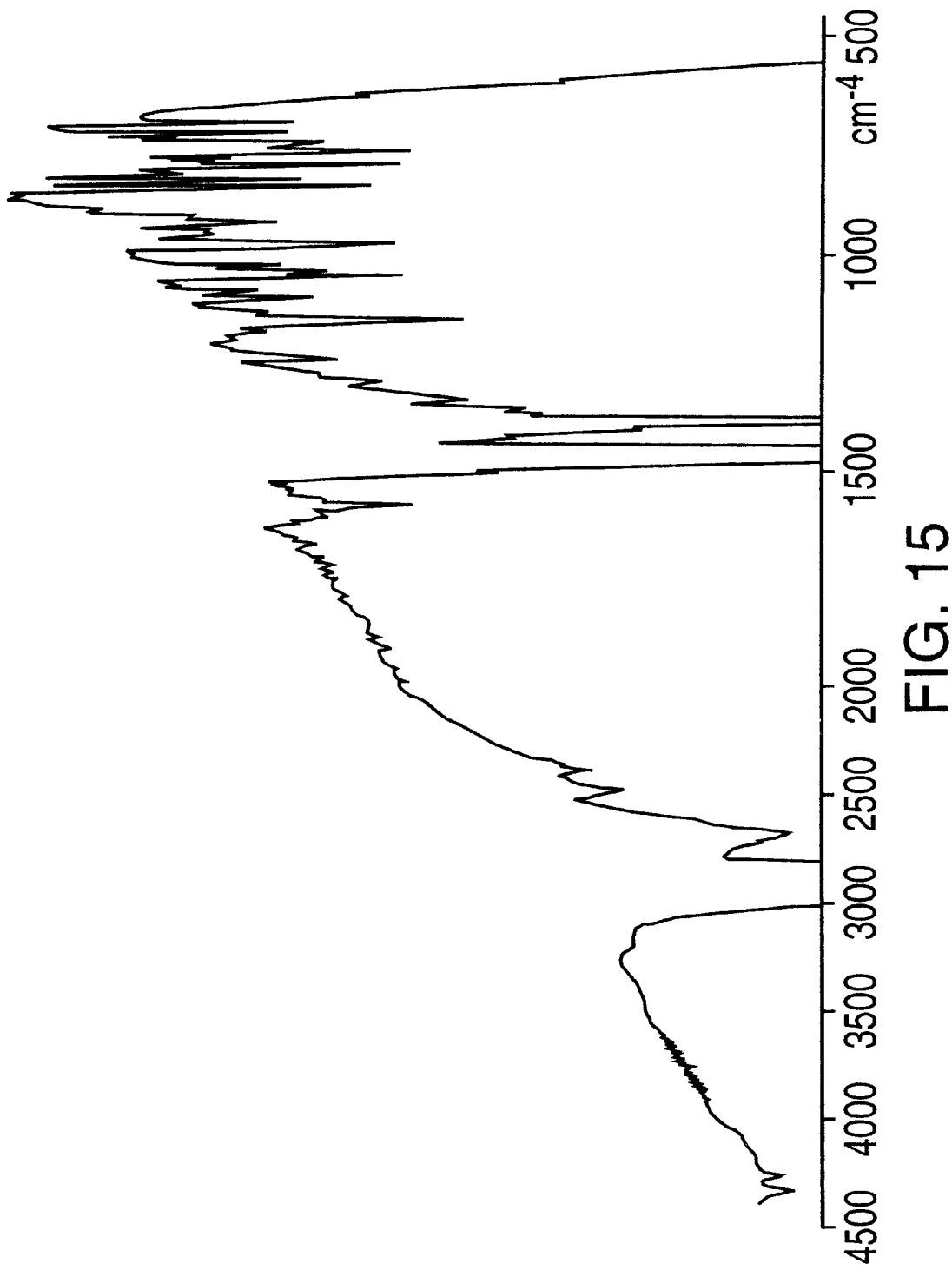
FIG. 15 is a characteristic infrared (IR) absorption spectrum of sertraline hydrochloride Form X.

The IR spectrum of Form X is characterized by the following bands: 742 $cm^{-1}$, 776 $cm^{-1}$, 806 $cm^{-1}$, 824 $cm^{-1}$, 1002 $cm^{-1}$, 1017 $cm^{-1}$, 1028 $cm^{-1}$, 1060 $cm^{-1}$, 1079 $cm^{-1}$, 1135 $cm^{-1}$, 1218 $cm^{-1}$, 1314 $cm^{-1}$, 1336 $cm^{-1}$, and 1560 $cm^{-1}$ as described in FIG. 15.

Figure 16:
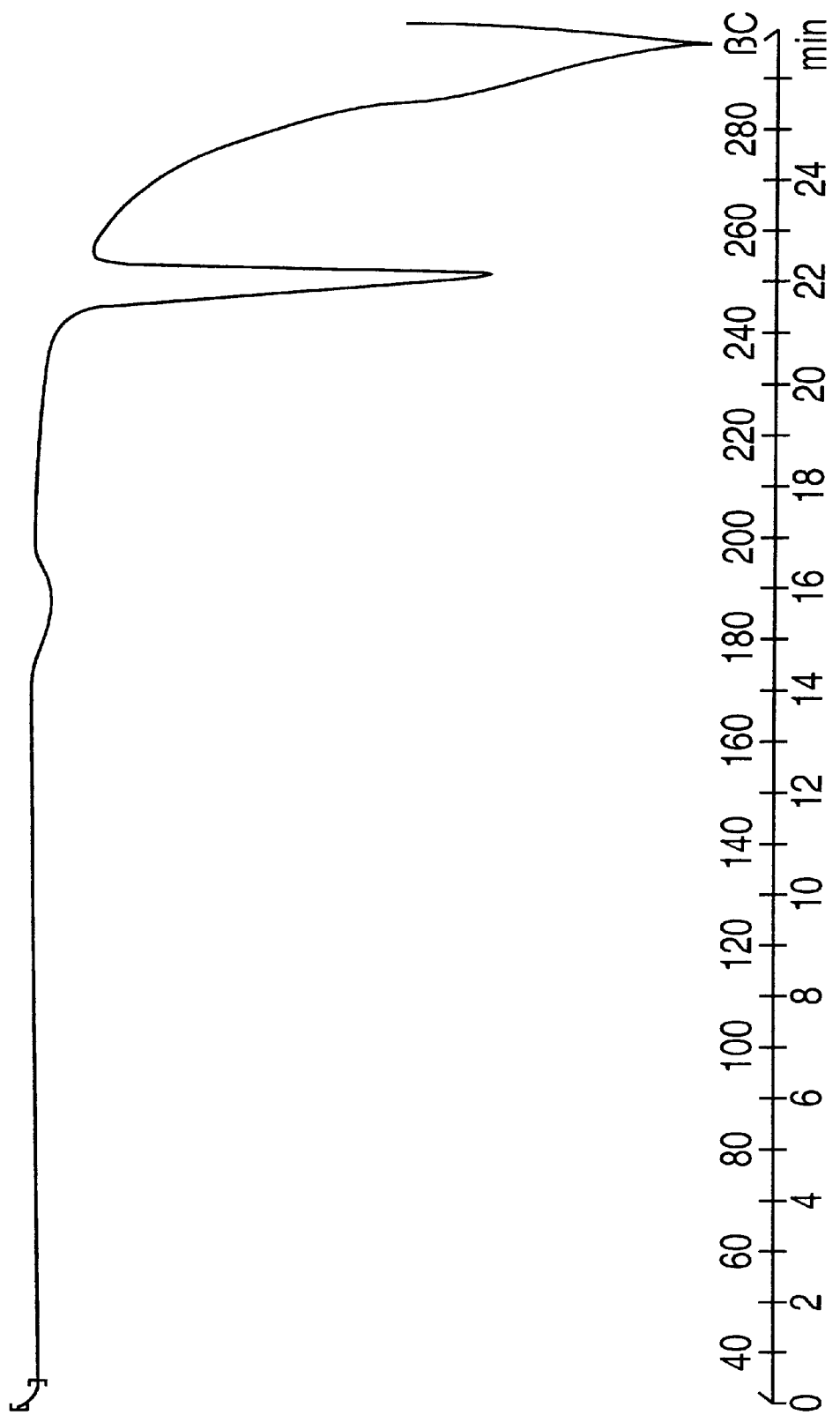
FIG. 16 is a characteristic differential scanning calorimetric (DSC) thermogram of sertraline hydrochloride Form X.

The DSC of Form X shows a small endotherm at about 190° C. followed by a melting endotherm at about 250° C. (see FIG. 16).

Form III

The present invention provides new processes for making sertraline hydrochloride Form III from sertraline hydrochloride Forms V and VI. In the conversion of sertraline hydrochloride Form V to sertraline hydrochloride Form III, Form V is heated to a temperature between about 150° C. and about 180° C. for about 3 hours to about 2 days to induce the formation of sertraline hydrochloride Form III. Heating for 24 hours is preferred. The reaction may be stirred. The method of the present invention has the advantage of using no solvent.

Amorphous Sertraline Hydrochloride

In an embodiment of the present invention, amorphous sertraline is made by dissolving sertraline hydrochloride in water or a water/alcohol mixture and drying the solution by the spray dryer technique. Amorphous sertraline hydrochloride may also be made by sublimation of sertraline hydrochloride.

The amorphous sertraline hydrochloride produced by methods of the present invention is characterized by a powder x-ray diffraction pattern having the typical broad featureless pattern without sharp peaks typical of amorphous materials. FIG. 2 is one such pattern.

Pharmaceutical Compositions Containing Sertraline Hydrochloride Polymorphs

In accordance with the present invention, these new crystalline forms of sertraline hydrochloride and known forms of sertraline hydrochloride prepared by the new methods disclosed herein may be prepared as pharmaceutical compositions that are particularly useful for the treatment of depression, obsessive-compulsive disorder and panic disorder. Such compositions comprise one of the new crystalline forms of sertraline hydrochloride with pharmaceutically acceptable carriers and/or excipients known to one of skill in the art.

For example, these compositions may be prepared as medicaments to be administered orally, parenterally, rectally, transdermally, bucally, or nasally. Suitable forms for oral administration include tablets, compressed or coated pills, dragees, sachets, hard or gelatin capsules, sub-lingual tablets, syrups and suspensions. Suitable forms of parenteral administration include an aqueous or non-aqueous solution or emulsion, while for rectal administration suitable forms for administration include suppositories with hydrophilic or hydrophobic vehicle. For topical administration the invention provides suitable transdermal delivery systems known in the art, and for nasal delivery there are provided suitable aerosol delivery systems known in the art.

Experimental

The powder X-ray diffraction patterns were obtained by methods known in the art using a Philips X-ray powder diffractometer, Goniometer model 1050/70 at a scanning speed of 2° per minute, with a Cu radiation of λ=1.5418 §.

The differential scanning calorimeter thermograms were obtained by methods known in the art using a DSC Mettler 821 Star°. The weight of the samples was less than 5 mg. The temperature range of scans was 30° C.–300° C. at a rate of 10° C./min. Samples were purged with nitrogen gas at a flow rate of 40 mL/min. Standard 40 μm aluminum crucibles were used having lids with three small holes.

The infrared spectra were obtained by methods known in the art using a Perkin Elmer FT-IR Paragon 1000 spectrometer. Samples were analyzed in Nujol mulls. Spectra were obtained at 4 cm$^{-1}$ resolution and 16 scans each.

EXAMPLES

The present invention will now be further explained in the following examples. However, the present invention should not be construed as limited thereby. One of ordinary skill in the art will understand how to vary the exemplified preparations to obtain the desired results.

Example 1

Preparation of Sertraline Base

Sertraline mandelate (5 g) was stirred at room temperature with 50 mL ethyl acetate. Aqueous sodium hydroxide was added dropwise until the sertraline mandelate was completely neutralized. The phases were separated and the organic phase was dried over MgSO$_4$ and filtered. The solvent was removed under reduced pressure resulting sertraline base as an oil (3.2 g).

Example 2

Preparation of Sertraline Hydrochloride Form VI and Form V

Sertraline base (25 g) was dissolved in methanol (125 mL) at room temperature. The solution was acidified with hydrogen chloride gas until pH 1.5 was reached. (Precipitation occurred during acidification.) The temperature rose to approximately 40° C. The slurry was allowed to cool to room temperature and stirred for about 2 hours. The solid was separated by filtration to give sertraline hydrochloride methanolate Form VI. Drying the product overnight gave sertraline hydrochloride Form V.

Example 3

Preparation of Sertraline Hydrochloride Form VI and Form V

Sertraline base (3.2 g) was dissolved in absolute ethanol (32 mL) at room temperature and then hydrogen chloride gas was bubbled in until pH 0.5 was reached. The temperature rose to 40° C. The slurry was allowed to cool to room temperature and stirred for about 16 hours. The solid was separated by filtration, and washed with ethanol (3×2 mL). FIG. 5 sets forth the X-ray diffraction pattern of the product (sertraline hydrochloride ethanolate Form VI) so obtained. Drying overnight at 50–60° C. of that product yielded 2.95 g (82%) of sertraline hydrochloride Form V.

Example 4

Preparation of Sertraline Hydrochloride Form V

Sertraline base (3 g) was dissolved in absolute ethanol (15 mL) at room temperature. A saturated solution of hydrogen chloride in isopropyl alcohol was added dropwise to reach a pH of 1.3. The resulting slurry was stirred at room temperature overnight. The solid was separated by filtration and dried overnight at 50–60° C. yielding 2.75 g (81. 8%) sertraline hydrochloride Form V.

Example 5

Preparation of Sertraline Hydrochloride Form V

Sertraline base (3 g) was dissolved in absolute ethanol (15.5 mL) at room temperature and then the solution was cooled to approximately 0° C. Hydrogen chloride gas was bubbled until pH 0.5 was reached. The temperature rose to approximately 7° C. Precipitation occurred and the slurry was stirred at about 10° C. for 2 hours. The solid was isolated by filtration, washed with ethanol and dried at approximately 50° C. The dried material (2.87 g, yield 82.7%) was sertraline hydrochloride Form V.

Example 6

Preparation of Sertraline Hydrochloride Form V

Sertraline base (3 g) was stirred with 35 mL water. The slurry was heated at ~70° C. and, while maintaining this temperature, concentrated hydrochloric acid was added until pH 1 was reached. During acidification, almost complete dissolution was observed followed by precipitation. The mixture was cooled to room temperature and stirred for 2 hours. The solid was isolated by filtration, washed with water and dried overnight at 50–60° C., yielding 3.23 g (96%) sertraline hydrochloride Form V.

Example 7

Preparation of Sertraline Hydrochloride Form V

Sertraline base (3 g) was dissolved in 10 mL absolute ethanol at 40° C. The solution was heated to 50–60° C. and concentrated hydrochloric acid 32% (1.2 mL) was added until pH ~1.3 was reached. Water (12 mL) was added. The resulting clear solution was concentrated to half its volume and was allowed to cool naturally to room temperature. The solid was isolated by filtration, washed with water and dried overnight at 50–60° C., yielding 3.18 g (94.65%) sertraline hydrochloride Form V.

Example 8

Preparation of Sertraline Hydrochloride Form V

Sertraline base (3.7 g) was dissolved in 18.5 mL absolute ethanol and the solution was heated to 60° C. Hydrogen chloride gas was bubbled through the ethanol solution until pH ~0.5 was reached. The mixture was cooled to room temperature and the stirring was continued for 2 hours. The solid obtained after filtration, washing with ethanol and drying at 50° C. was sertraline hydrochloride Form V (3.16 g, yield 76%).

Example 9

Preparation of Sertraline Hydrochloride Form V

Sertraline free base was dissolved in ethanol absolute and the solution was acidified with hydrogen chloride gas to about pH 3. Precipitation occurs and the slurry was stirred at room temperature for 2 hours. The resulting solid was filtered, washed with ethanol and dried to yield sertraline hydrochloride Form V.

Example 10

Preparation of Sertraline Hydrochloride Form V

Sertraline free base (13.3 g) was dissolved in absolute ethanol (60 mL) and was added dropwise over one hour to ethanol (20 mL) containing hydrogen chloride (17.5 g) at 35° C. with precipitation. After 2 hours, the solid was filtrated, washed with ethanol and dried at about 80° C. to yield sertraline hydrochloride Form V (12.9 g, yield 87%).

Example 11

Preparation of Sertraline Hydrochloride Form V

Anhydrous sertraline hydrochloride (2 g) was stirred with 14 mL absolute ethanol and heated to reflux to obtain a clear solution. The solution was seeded with sertraline hydrochloride Form V and cooled naturally to room temperature. Massive precipitation was observed at about 50° C. The slurry was stirred at room temperature during 2 hours. The solid was filtered, washed with ethanol (3 mL) and dried overnight at 50–60° C. yielding 1.71 g (85.5%) of sertraline hydrochloride Form V.

Example 12

Preparation of Sertraline Hydrochloride Form V

Sertraline hydrochloride ethanolate (Form VI) (40 g) in 400 mL water was heated to 80° C. and complete dissolution was obtained. The pH was adjusted to approximately one with hydrochloric acid and the solution was naturally cooled to room temperature and stirred for 2 hours. The solid was filtered and dried at 50° C. for approximately 16 hours, yielding sertraline hydrochloride Form V.

Example 13

Preparation of Sertraline Hydrochloride Form V

Sertraline hydrochloride ethanolate (Form VI) (2 g) was mechanically stirred with ethanol (0.5 mL) at room temperature for 40 hours. The resulting solid was sertraline hydrochloride Form V.

Table 1 sets forth a summary of additional experiments conducted generally following procedures described above.

TABLE 1

PREPARATION OF SERTRALINE HCL - FORM V

| Exp't | Method of Crystallization | XRD | Yield (%) |
|---|---|---|---|
| | SERTRALINE BASE AS STARTING MATERIAL | | |
| A | Methanol/HCl gas | V | 78.7 |
| B | Methanol/HCl gas | V | 69 |
| C | Methanol/HCl aqueous | V | 87.8 |
| D | Ethanol/HCl gas | V | 80.9 |
| E | Water/HCl aqueous | V | 96 |
| F | Hexane/Isopropyl alcohol/HCl gas | V | 89.9 |
| G | Methanol/HCl aqueous/water | V | 89 |
| H | Isopropyl alcohol/HCl aqueous/water | V | 78 |
| I | Ethanol/HCl aqueous/evaporation of ethanol | V | 96.1 |
| J | Ethyl acetate/HCl aqueous/water/evaporation of ethyl acetate | V | 96.1 |
| K | Ethanol/isopropyl alcohol/HCl gas | V | 81.8 |
| L | Methanol/isopropyl alcohol/HCl gas | V | 82.4 |

TABLE 1-continued

PREPARATION OF SERTRALINE HCL - FORM V

| Exp't | Method of Crystallization | XRD | Yield (%) |
|---|---|---|---|
| | SERTRALINE HCl AS STARTING MATERIAL | | |
| M | Methanol (Form I and amorphous) | V | 60 |
| N | Ethanol (Form V) | V | 85.5 |
| O | Isopropyl alcohol/water (Form V) | V | 28 |

PXRD = powder x-ray diffraction.

Example 14

Preparation of Sertraline Hydrochloride Form VII 1.003 g Sertraline hydrochloride Form V was stirred for 24 hours at room temperature in 20 mL water (HPLC grade). At the end of the stirring the mixture looked like a jelly suspension. The suspension was filtrated and the compound obtained was kept at cold conditions (4° C.) until analyzed by x-ray diffraction.

Example 15

Preparation of Sertraline Hydrochloride Form VII from Sertraline Hydrochloride Form VI A solution of sertraline hydrochloride ethanolate (Form VI) (40 g) in water (400 mL) was heated at 80° C. and complete dissolution of sertraline hydrochloride ethanolate (Form VI) was obtained. The pH was adjusted to about 1 and the solution was allowed to cool to room temperature and then stirred for 2 additional hours. The solid was isolated by filtration and washed with water to yield sertraline hydrochloride Form VII.

Sertraline hydrochloride Form VII dried overnight at 80° C. forms sertraline hydrochloride Form V.

Example 16

Figure 10:
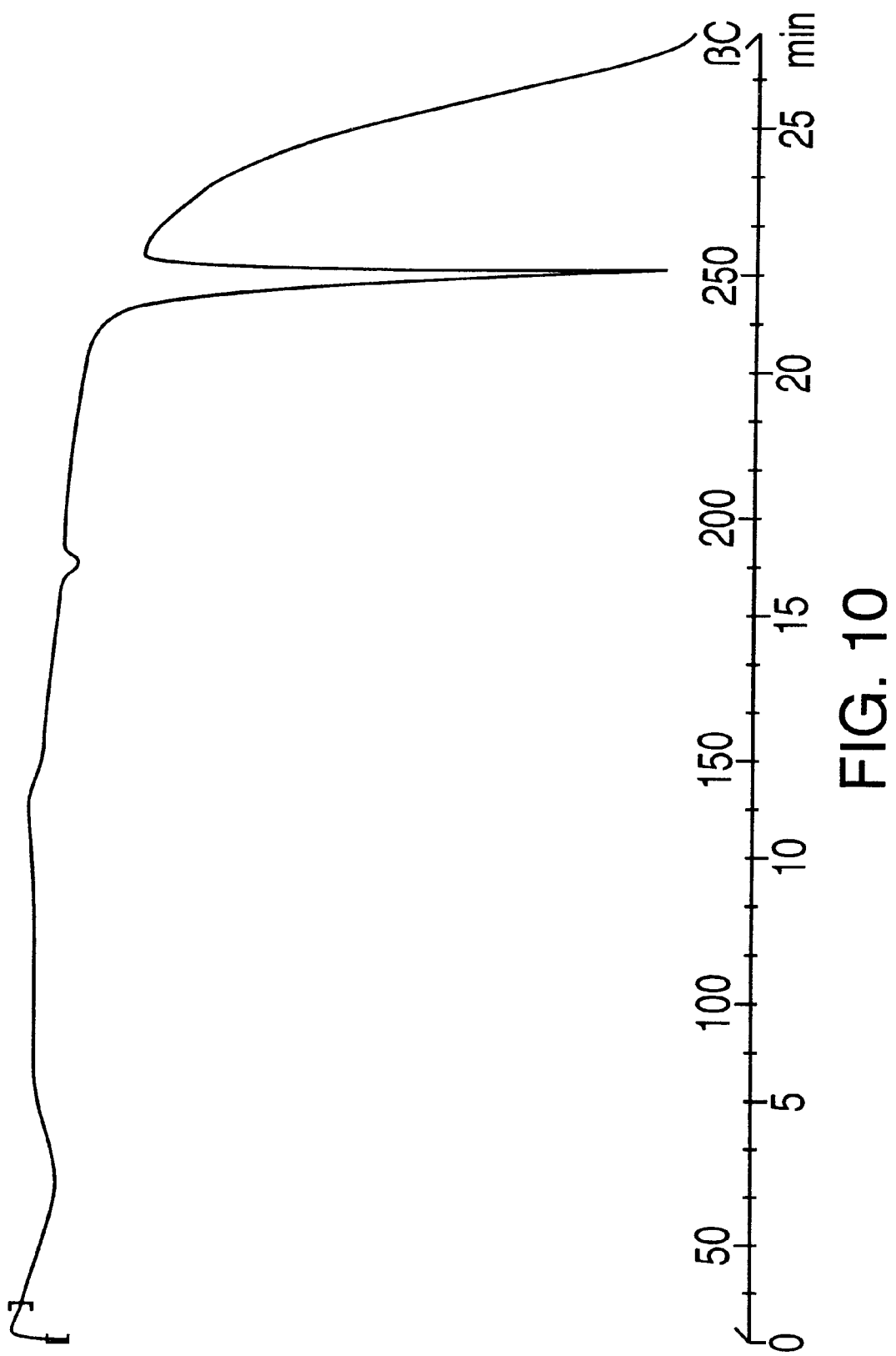
FIG. 10 is a characteristic differential scanning calorimetric (DSC) thermogram of sertraline hydrochloride Form IX.

Preparation of Sertraline Hydrochloride Forms VIII and IX from Sertraline Base Sertraline base (2.7 g) was suspended in 27 mL of water. This mixture was heated to 80° C. and treated with hydrochloric acid until about pH 1 was reached. A clear solution was obtained, which on cooling gave a precipitate. After 2 hours stirring at room temperature the solid was isolated by filtration. This solid was characterized by powder x-ray diffraction (see FIG. 3, Form VIII). Drying for 24 hours at ~50° C. yielded 2.32 g (76.8%) of sertraline hydrochloride Form IX, characterized by powder x-ray diffraction, infrared absorption, differential scanning calorimetry, and thermal gravimetric analysis as set forth above and depicted in FIGS. 8, 10, and 12.

Example 17

Preparation of Sertraline Hydrochloride Form VIII

Sertraline hydrochloride ethanolate (Form VI) (40 g) was stirred with water (80 ml.) for 1 hour at room temperature. The slurry was filtrated and washed with water to yield sertraline hydrochloride hydrate Form VIII.

Example 18

Preparation of Sertraline Hydrochloride Form VIII from Sertraline Hydrochloride Form II Sertraline hydrochloride Form 11 (0.4 g) and water (8 mL) were stirred at room temperature over night. The solid was filtrated to yield sertraline hydrochloride hydrate Form VIII.

Example 19

Preparation of Sertraline Hydrochloride Form X

In a 0.1 liter three-necked bottom round flask equipped with a mechanical stirrer, a condenser and a thermometer, 30 mL benzyl alcohol is added to 10 g sertraline hydrochloride. The suspension is heated to 100° C. when a clear solution is obtained. The solution is cooled 2 hours to 25° C. and the precipitate is filtered and washed with benzyl alcohol. After drying under vacuum at 80° C. for 24 hours, 6.2 g of sertraline hydrochloride Form X is obtained (yield 62%). The sertraline hydrochloride Form X was characterized by powder x-ray diffraction and infrared absorption analysis as set forth above and in FIG. 14 and FIG. 15.

Example 20

Preparation of Sertraline Hydrochloride Ethanolate Form VI by Reslurry of Form I Sertraline hydrochloride Form I (1 g) and absolute ethanol (20 mL) were stirred at room temperature for 24 hours. Filtration of the mixture yielded sertraline hydrochloride ethanolate-Form VI.

Example 21

Preparation of Sertraline Hydrochloride Ethanolate Form VI by Reslurry of Form II Sertraline hydrochloride Form II (1 g) and absolute ethanol (20 mL) were stirred at room temperature for 24 hours. Filtration of the mixture yielded sertraline hydrochloride ethanolate Form VI.

Example 22

Preparation of Sertraline Hydrochloride Ethanolate Form VI by Reslurry of Form V Sertraline hydrochloride Form V (1 g) and ethanol absolute (20 mL) were stirred at room temperature for 24 hrs. Filtration of the mixture yielded sertraline hydrochloride ethanolate Form VI.

Example 23

Preparation of Amorphous Sertraline Hydrochloride

Sertraline free base (10 g) was dissolved in ethyl acetate (690 mL). At room temperature, ether (690 mL) was added to the sertraline ethyl acetate solution and the solution was acidified with HCl gas to about pH 0.5. The resulting gelatinous suspension was stirred at room temperature over night. Filtration and air drying of the suspension yielded amorphous sertraline hydrochloride (9.39 g, yield 83.8%).

Example 24

Preparation of Sertraline Hydrochloride Form III from Form V

Sertraline hydrochloride Form V was heated at 150° C. in a reactor under mechanical stirring for 24 hrs. The resulting material obtained was sertraline hydrochloride Form III.

Example 25

Preparation of Sertraline Hydrochloride Form III from Form VI

Sertraline hydrochloride form VI was heated to 180° C. for 24 hours. The dried material is sertraline hydrochloride Form III.

Example 26

Preparation of Sertraline Hydrochloride Form III from Form V

Sertraline hydrochloride Form V was heated at a temperature >180° C. for 24 hours. The resulting material was sertraline hydrochloride Form III.

Example 27

Preparation of Amorphous Sertraline Hydrochloride

Sertraline hydrochloride Form V (10 g) was dissolved in water (2L) and this solution was dried by the spray dryer technique. The material obtained in this way is Sertraline hydrochloride amorphous.

Example 28

Preparation of Amorphous Sertraline Hydrochloride by Sublimation

Sertraline hydrochloride Form I was sublimated at 190–200° C., at a vacuum of 30–0.1 mm Hg, using a laboratory-type sublimator. The resulting material was amorphous sertraline hydrochloride.

A similar procedure starting from Form V also gave amorphous sertraline hydrochloride.

Example 29

Preparation of Sertraline Hydrochloride Form V from Amorphous Sertraline Hydrochloride Sertraline hydrochloride amorphous was heated to 80° C. for 24 hours. The resulting product was sertraline hydrochloride Form V.

It should be understood that some modification, alteration and substitution is anticipated and expected from those skilled in the art without departing from the teachings of the invention. Accordingly, it is appropriate that the following claims be construed broadly and in a manner consistent with the scope and spirit of the invention.

What is claimed is:

1. A process for making sertraline hydrochloride Form V comprising the steps of:
   (a) dissolving or suspending sertraline hydrochloride in a suitable solvent;
   (b) removing the solvent; and
   (c) drying to form sertraline hydrochloride Form V.

2. The process of claim 1, wherein the solvent is selected from the group consisting of methanol, ethanol, water, 1-methoxy-2-propanol, trichloroethane, and isopropyl alcohol, and mixtures thereof.

3. The process of claim 2, wherein the solvent is water.

4. The process of claim 3, wherein the step of drying to form sertraline hydrochloride Form V is achieved by spray drying.

5. The process of claim 1, further comprising the step of seeding the solution with sertraline hydrochloride Form V.

6. A process for making sertraline hydrochloride Form V comprising the steps of:
   (a) dissolving or suspending sertraline base in a solvent;
   (b) adding hydrogen chloride gas to the solvent to reduce the pH of the solution or suspension; and
   (c) isolating sertraline hydrochloride Form V from the solution or suspension.

7. The process of claim 6 wherein the pH of the solution or suspension of sertraline base and hydrogen chloride is about 0 to about 4.

8. The process of claim 6 wherein the solvent is selected from the group consisting of methanol, ethanol, water, ethyl acetate, isopropyl alcohol, ether, hexane, and toluene, and mixtures thereof.

9. The process of claim 8 wherein the solvent is ether.

10. The process of claim 8 wherein the solvent is water.

11. The process of claim 10 wherein the step of isolating sertraline hydrochloride Form V is done by spray drying the solution or suspension.

12. A process for making sertraline hydrochloride Form V comprising the step of drying sertraline hydrochloride Form VII at about 80° C.

13. A process for making sertraline hydrochloride Form V comprising the steps of:
   (a) dissolving or suspending sertraline hydrochloride in water;
   (b) adding a sufficient amount of hydrogen chloride to facilitate precipitation of sertraline hydrochloride;
   (c) removing the water; and
   (d) isolating sertraline hydrochloride Form V.

14. A process for making sertraline hydrochloride Form VI comprising the steps of:
   (a) dissolving sertraline base in a solvent;
   (b) adding hydrogen chloride to the solvent; and
   (c) isolating sertraline hydrochloride Form VI without further drying.

15. The process of claim 14 wherein the isolation step comprises precipitation of sertraline hydrochloride Form VI followed by filtration.

16. The process of claim 14 wherein the solvent is at least one solvent selected from the group consisting of ethanol, methanol, or mixtures of methanol or ethanol with water.

17. A process for making sertraline hydrochloride Form VI comprising the steps of:
   (a) suspending sertraline hydrochloride Form I, II or V in ethanol or methanol;
   (b) stirring for a time sufficient to induce the transformation of sertraline hydrochloride to sertraline hydrochloride Form VI; and
   (c) isolating sertraline hydrochloride Form VI.

18. A process for making sertraline hydrochloride Form VIII comprising the steps of:
   (a) suspending sertraline base in water;
   (b) adding hydrogen chloride to the water; and
   (c) filtrating the precipitate so obtained without further drying.

19. A process for making sertraline hydrochloride Form VIII comprising the steps of:
   (a) suspending or dissolving sertraline hydrochloride ethanolate Form VI or sertraline hydrochloride Form II in water or a mixture of water and isopropyl alcohol; and
   (b) isolating sertraline hydrochloride Form VIII.

20. A process for making sertraline hydrochloride Form III comprising the steps of:
   (a) heating sertraline hydrochloride Form V or Form VI to a temperature sufficient, and for a time sufficient, to induce the transformation of sertraline hydrochloride Form V or Form VI to sertraline hydrochloride Form III; and
   (b) isolating sertraline hydrochloride Form III.

21. The process of claim 20 wherein the temperature is between about 150° C. and about 180° C.

22. A process for making amorphous sertraline hydrochloride comprising the steps of:
   (a) suspending or dissolving sertraline base in a solvent selected from the group consisting of ether, toluene and t-butyl-methyl ether, and mixtures thereof;
   (b) adding hydrogen chloride gas; and
   (c) isolating amorphous sertraline hydrochloride.

23. The process of claim 2, wherein the solvent is 1-methoxy-2-propanol.

24. A process for making sertraline hydrochloride Form V comprising the steps of :
   (a) dissolving or suspending sertraline base in a solvent;
   (b) adding hydrochloric acid to the solvent to reduce the pH of the solution or suspension; and
   (c) isolating sertraline hydrochloride Form V form the solution or suspension.

25. The process of claim 24, wherein the pH of the solution or suspension of sertraline base and hydrogen chloride is about 0 to about 4.

26. The process of claim 24 wherein the solvent is selected from the group consisting of methanol, ethanol, water, ethyl acetate, isopropyl alcohol, ether, hexane, and toluene, and mixtures thereof.

27. The process of claim 26 wherein the solvent is ether.

28. The process of claim 26 wherein the solvent is water.

29. The process of claim 28 wherein the step of isolating sertraline hydrocloride Form V is done by spray drying the solution or suspension.

* * * * *